(12) United States Patent
Merchant et al.

(10) Patent No.: US 7,476,331 B2
(45) Date of Patent: Jan. 13, 2009

(54) COMPOSITIONS COMPRISING 1,1,1,2,2,3,4,5,5,6,6,7,7,7-TETRADECAFLUOROHEPTANE AND USES THEREOF

(75) Inventors: Abid N. Merchant, Wilmington, DE (US); Barbara Haviland Minor, Elkton, MD (US); Shoeb A. Moiyadi, San Jose, CA (US); Melodie A. Schweitzer, Wilmington, DE (US); Allen Capron Sievert, Elkton, MD (US)

(73) Assignee: E I Du Pont Nemours and Company, Wilmington, DE (US)

( * ) Notice: Subject to any disclaimer, the term of this patent is extended or adjusted under 35 U.S.C. 154(b) by 461 days.

(21) Appl. No.: 11/347,391

(22) Filed: Feb. 3, 2006

(65) Prior Publication Data

US 2006/0180785 A1    Aug. 17, 2006

Related U.S. Application Data

(60) Provisional application No. 60/651,720, filed on Feb. 9, 2005, provisional application No. 60/651,687, filed on Feb. 9, 2005, provisional application No. 60/651,575, filed on Feb. 9, 2005.

(51) Int. Cl.
    *C09K 5/04*    (2006.01)
(52) U.S. Cl. .............................. 252/68; 252/67; 510/177

(58) Field of Classification Search ................... 252/67, 252/68; 510/177
See application file for complete search history.

(56) References Cited

U.S. PATENT DOCUMENTS

| 5,065,990 | A | 11/1991 | Durfee |
| 5,171,902 | A | 12/1992 | Krespan et al. |
| 5,219,651 | A | 6/1993 | Shoji et al. |
| 5,723,701 | A | 3/1998 | Krespan |
| RE36,951 | E | 11/2000 | Cooper et al. |
| 6,506,950 | B1 | 1/2003 | Krespan |
| 2003/0134757 | A1 | 7/2003 | Milbrath et al. |

FOREIGN PATENT DOCUMENTS

| WO | WO 99/63043 | * | 12/1999 |
| WO | WO 2004/000977 A1 | | 12/2003 |
| WO | WO 2005/008819 A2 | | 1/2005 |
| WO | WO 2006/086683 A3 | * | 8/2006 |

* cited by examiner

*Primary Examiner*—John R Hardee
(74) *Attorney, Agent, or Firm*—Hanxing Zheng

(57) ABSTRACT

The present invention relates to compositions comprising HFC-63-14mcee. The compositions may be azeotropic or azeotrope-like and are useful in cleaning applications, as a defluxing agent, for removing oils or residues from a surface, depositing or removing lubricants from a surface, and as refrigerants or heat transfer fluids in refrigeration systems, air-conditioners and heat pumps.

18 Claims, No Drawings

COMPOSITIONS COMPRISING
1,1,1,2,2,3,4,5,5,6,6,7,7,7-TETRADECA
FLUOROHEPTANE AND USES THEREOF

CROSS REFERENCE(S) TO RELATED
APPLICATION(S)

This application claims the priority benefit of U.S. Provisional Application 60/651,720, filed Feb. 9, 2005, U.S. Provisional Application 60/651,687, filed Feb. 9, 2005, and U.S. Provisional Application 60/651,575, filed Feb. 9, 2005.

BACKGROUND OF THE INVENTION

1. Field of the Invention

The present invention relates to compositions comprising 1,1,1,2,2,3,4,5,5,6,6,7,7,7-tetradecafluoroheptane (HFC-63-14mcee). These compositions include binary and ternary azeotropic or azeotrope-like compositions. These compositions are useful in cleaning applications, as a defluxing agent, for removing oils or residues from a surface, depositing or removing lubricants on or from a surface, and as refrigerants or heat transfer fluids in refrigeration systems, air-conditioners and heat pumps.

2. Description of Related Art

As electronic circuit boards evolve toward increased circuit and component densities, thorough board cleaning becomes a more critical process step. After soldering, the flux-residues are often removed with an organic solvent. Defluxing solvents should have low toxicity and have high solvency power, so that the flux and flux-residues can be removed without damaging the substrate being cleaned. Further, other types of residue, such as oils and greases, must be effectively removed from these devices for optimal performance in use.

Additionally, fluorolubricants are widely used in the magnetic disk drive industry to decrease the friction between a read-write head and a digital disk to reduce wear and minimize disk failure. Deposition of these fluorolubricants on the disk surface requires a solvent capable of dissolving the fluorolubricant and forming a substantially uniform coating of fluorolubricant when evaporated.

Alternative, non-ozone depleting solvents have become available since the elimination of nearly all previous chlorofluorocarbons (CFCs) and hydrochlorofluorocarbons (HCFCs) as a result of the Montreal Protocol. While boiling point, flammability and solvent power characteristics can often be adjusted by preparing solvent mixtures, these mixtures are often unsatisfactory in the commonly used cleaning equipment because they fractionate to an undesirable degree during use. Such solvent mixtures also fractionate during solvent distillation, which makes it virtually impossible to recover a solvent mixture with the original composition.

Azeotropic solvent mixtures may possess the properties needed for these cleaning (defluxing or degreasing) applications and other cleaning agent needs. Azeotropic mixtures exhibit either a maximum or a minimum boiling point and they do not fractionate on boiling. The constant composition in use assures that the composition will not change during use and that solvency properties will remain constant as well.

The present invention provides azeotropic and azeotrope-like compositions useful in cleaning semiconductor chips and circuit boards and processes for removing oil and grease residues from surfaces.

The present azeotropic or azeotrope-like compositions are also useful as refrigerants or heat transfer fluids in refrigeration, air conditioning and heat pump systems.

BRIEF SUMMARY OF THE INVENTION

The present invention relates to a method for depositing fluorolubricant on a surface, said method comprising:
a) combining fluorolubricant with solvent, that solvent being HFC-63-14mcee, to form a lubricant-solvent combination; and
b) contacting said lubricant-solvent combination with said surface;
c) evaporating said HFC-63-14mcee from said surface, to form a fluorolubricant coating.

The present invention further relates to a method for solubilizing a fluorolubricant, said method comprising contacting HFC-63-14mcee with a fluorolubricant.

The present invention further relates to a method for removing contaminants from a surface comprising:
a) contacting the surface with solvent, that solvent comprising HFC-63-14mcee; and
b) recovering the surface from the solvent.

The present invention further relates to azeotropic or azeotrope-like cleaning compositions comprising:
a) HFC-63-14mcee;
b) trans-1,2-dichloroethylene; and
c) at least one alcohol selected from the group consisting of methanol, ethanol, and isopropanol.

The present invention further relates to an azeotropic or azeotrope-like composition selected from the group consisting of:
about 38 to about 83 weight percent HFC-63-14mcee and about 62 to about 17 weight percent cyclohexane;
about 39 to about 82 weight percent HFC-63-14mcee and about 61 to about 18 weight percent 2,2,3-trimethylbutane;
about 39 to about 82 weight percent HFC-63-14mcee and about 61 to about 18 weight percent 2,4-dimethylpentane;
about 42 to about 84 weight percent HFC-63-14mcee and about 58 to about 16 weight percent 3,3-dimethylpentane;
about 45 to about 86 weight percent HFC-63-14mcee and about 55 to about 14 weight percent 2,3-dimethylpentane;
about 45 to about 86 weight percent HFC-63-14mcee and about 55 to about 14 weight percent 2-methylhexane;
about 46 to about 86 weight percent HFC-63-14mcee and about 54 to about 14 weight percent 3-methylhexane;
about 51 to about 89 weight percent HFC-63-14mcee and about 49 to about 11 weight percent n-heptane;
about 48 to about 89 weight percent HFC-63-14mcee and about 52 to about 11 weight percent methylcyclohexane;
about 59 to about 99 weight percent HFC-63-14mcee and about 41 to about 1 weight percent toluene;
about 49 to about 88 weight percent HFC-63-14mcee and about 51 to about 12 weight percent isooctane;
about 62 to about 99 weight percent HFC-63-14mcee and about 38 to about 11 weight percent n-octane;
about 1 to about 68 weight percent HFC-63-14mcee and about 99 to about 32 weight percent 2-bromopropane;
about 19 to about 74 weight percent HFC-63-14mcee and about 81 to about 26 weight percent 1-bromopropane;
about 36 to about 82 weight percent HFC-63-14mcee and about 64 to about 18 weight percent 1,2-dichloroethane;
about 1 to about 62 weight percent HFC-63-14mcee and about 99 to about 38 weight percent 1,1-dichloroethane;
about 39 to about 85 weight percent HFC-63-14mcee and about 61 to about 15 weight percent fluorobenzene;
about 36 to about 99 weight percent HFC-63-14mcee and about 64 to about 1 weight percent methylene bromide;
about 35 to about 80 weight percent HFC-63-14mcee and about 65 to about 20 weight percent trichloroethylene;

about 53 to about 99 weight percent HFC-63-14mcee and about 47 to about 1 weight percent tetrachloroethylene;

about 70 to about 99 weight percent HFC-63-14mcee and about 30 to about 1 weight percent chlorobenzene;

about 1 to about 72 weight percent HFC-63-14mcee and about 99 to about 28 weight percent cis-1,2-dichloroethylene;

about 1 to about 68 weight percent HFC-63-14mcee and about 99 to about 32 weight percent trans-1,2-dichloroethylene;

about 1 to about 93 weight percent HFC-63-14mcee and about 99 to about 7 weight percent methanol;

about 58 to about 92 weight percent HFC-63-14mcee and about 42 to about 8 weight percent ethanol;

about 69 to about 94 weight percent HFC-63-14mcee and about 31 to about 6 weight percent n-propanol;

about 58 to about 91 weight percent HFC-63-14mcee and about 42 to about 9 weight percent isopropanol;

about 52 to about 88 weight percent HFC-63-14mcee and about 48 to about 12 weight percent 2-methyl-2-propanol;

about 63 to about 92 weight percent HFC-63-14mcee and about 37 to about 8 weight percent 2-methyl-2-butanol;

about 64 to about 93 weight percent HFC-63-14mcee and about 36 to about 7 weight percent 2-butanol;

about 70 to about 95 weight percent HFC-63-14mcee and about 30 to about 5 weight percent isobutanol;

about 75 to about 99 weight percent HFC-63-14mcee and about 25 to about 1 weight percent n-butanol;

about 77 to about 97 weight percent HFC-63-14mcee and about 23 to about 3 weight percent 2-methoxyethanol;

about 1 to about 84 weight percent HFC-63-14mcee and about 99 to about 16 weight percent 2,2,2-trifluoroethanol;

about 1 to about 82 weight percent HFC-63-14mcee and about 99 to about 18 weight percent 2,2,3,3,3-pentafluoro-1-propanol;

about 59 to about 99 weight percent HFC-63-14mcee and about 41 to about 1 weight percent 2,2,3,3-tetrafluoro-1-propanol;

about 1 to about 64 weight percent HFC-63-14mcee and about 99 to about 36 weight percent 1,1,1,3,3,3-hexafluoro-2-propanol;

about 46 to about 91 weight percent HFC-63-14mcee and about 54 to about 9 weight percent acetonitrile;

about 61 to about 96 weight percent HFC-63-14mcee and about 39 to about 4 weight percent propionitrile;

about 71 to about 99 weight percent HFC-63-14mcee and about 29 to about 1 weight percent butyronitrile;

about 64 to about 99 weight percent HFC-63-14mcee and about 36 to about 1 weight percent n-methylmorpholine;

about 74 to about 99 weight percent HFC-63-14mcee and about 26 to about 1 weight percent morpholine;

about 34 to about 83 weight percent HFC-63-14mcee and about 66 to about 17 weight percent ethyl acetate;

about 35 to about 83 weight percent HFC-63-14mcee and about 65 to about 17 weight percent methyl propionate;

about 38 to about 84 weight percent HFC-63-14mcee and about 62 to about 16 weight percent n-propyl formate;

about 46 to about 89 weight percent HFC-63-14mcee and about 54 to about 11 weight percent dimethyl carbonate;

about 44 to about 86 weight percent HFC-63-14mcee and about 56 to about 14 weight percent isopropyl acetate;

about 53 to about 91 weight percent HFC-63-14mcee and about 47 to about 9 weight percent isobutyl formate;

about 53 to about 91 weight percent HFC-63-14mcee and about 47 to about 9 weight percent ethyl propionate;

about 55 to about 92 weight percent HFC-63-14mcee and about 45 to about 8 weight percent n-propyl acetate;

about 56 to about 93 weight percent HFC-63-14mcee and about 44 to about 7 weight percent methyl n-butyrate;

about 59 to about 99 weight percent HFC-63-14mcee and about 41 to about 1 weight percent butyl formate;

about 68 to about 99 weight percent HFC-63-14mcee and about 32 to about 1 weight percent diethyl carbonate;

about 1 to about 99 weight percent HFC-63-14mcee and about 99 to about 1 weight percent 2-butanone;

about 1 to about 99 weight percent HFC-63-14mcee and about 99 to about 1 weight percent 3-methyl-2-butanone;

about 1 to about 99 weight percent HFC-63-14mcee and about 99 to about 1 weight percent 2-bromo-1,1,1,4,4,5,5,5-octafluoro-2-(trifluoromethyl)-3 pentanone;

about 1 to about 99 weight percent HFC-63-14mcee and about 99 to about 1 weight percent 1,1,1,2,2,3,4,5,5,5-decafluoro-3-methoxy-4-(trifluoromethyl)-pentane;

about 47 to about 99 weight percent HFC-63-14mcee and about 53 to about 1 weight percent nitromethane;

about 45 to about 85 weight percent HFC-63-14mcee and about 55 to about 15 weight percent 1,2-dimethoxyethane;

about 50 to about 87 weight percent HFC-63-14mcee and about 50 to about 13 weight percent 2,2-dimethyl-1,3-dioxolane;

about 1 weight percent to about 68 weight percent HFC-63-14mcee, about 1 weight percent to about 98 weight percent $C_4F_9OCH_3$, and about 1 weight percent to about 98 weight percent trans-1,2-dichloroethylene;

about 1 weight percent to about 68 weight percent HFC-63-14mcee, about 1 weight percent to about 71 weight percent $C_4F_9OC_2H_5$, and about 28 weight percent to about 98 weight percent trans-1,2-dichloroethylene; and about 1 weight percent to about 68 weight percent HFC-63-14mcee, about 1 weight percent to about 71 weight percent $C_4F_9OC_2H_5$, about 28 weight percent to about 98 weight percent trans-1,2-dichloroethylene, and about 1 weight percent to about 30 weight percent methanol.

DETAILED DESCRIPTION OF THE INVENTION

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The fluorolubricants of the present invention comprise perfluoropolyether (PFPE) compounds, or lubricant comprising X-1P®, which is a phosphazene-containing disk lubricant. These perfluoropolyether compounds are sometimes referred to as perfluoroalkylethers (PFAE) or perfluoropolyalkylethers (PFPAE). These PFPE compounds range from simple perfluorinated ether polymers to functionalized perfluorinated ether polymers. PFPE compounds of different varieties that may be useful as fluorolubricant in the present invention are available from several sources. Useful fluorolubricants for the present inventive method include but are not limited to Krytox® GLP 100, GLP 105 or GLP 160 (E. I. du Pont de Nemours & Co., Fluoroproducts, Wilmington, Del., 19898, USA); Fomblin® Z-Dol 2000, 2500 or 4000, Z-Tetraol, or Fomblin® AM 2001 or AM 3001 (sold by Solvay Solexis S.p.A., Milan, Italy); Demnum™ LR-200 or S-65 (offered by Daikin America, Inc., Osaka, Japan); X-1P® (a partially fluorinated hexaphenoxy cyclotriphosphazene disk lubricant available from Quixtor Technologies Corporation, a subsidiary of Dow Chemical Co, Midland, Mich.); and mixtures thereof. The Krytox® lubricants are perfluoroalkylpolyethers having the general structure $F(CF(CF_3)CF_2O)_n$—$CF_2CF_3$, wherein n ranges from 10 to 60. The Fomblin® lubricants are functionalized perfluoropolyethers that range in molecular weight from 500 to 4000 atomic mass units and have general formula X—$CF_2$—O$(CF_2$—$CF_2$—O$)_p$—$(CF_2O)_q$—$CF_2$—X, wherein X may be —$CH_2OH$, $CH_2(O$—$CH_2$—$CH_2)_nOH$, $CH_2OCH_2CH(OH)CH_2OH$ or —$CH_2O$—$CH_2$-piperonyl. The Demnum™ oils are perfluoropolyether-based oils ranging in molecular weight from 2700 to 8400 atomic mass units.

The fluorolubricants of the present invention may additionally comprise additives to improve the properties of the fluorolubricant. X-1P®, which may serve as the lubricant itself, is often added to other lower cost fluorolubricants in order to increase the durability of disk drives by passivating Lewis acid sites on the disk surface responsible for PFPE degradation.

Other common lubricant additives may be used in the fluorolubricants of the present inventive methods.

The fluorolubricants of the present invention may further comprise Z-DPA (Hitachi Global Storage Technologies, San Jose, Calif.), a PFPE terminated with dialkylamine endgroups. The nucleophilic end-groups serve the same purpose as X1P®, thus providing the same stability without any additive.

The surface on which the fluorolubricant may be deposited is any solid surface that may benefit from lubrication. Semiconductor materials such as silica disks, metal or metal oxide surfaces, vapor deposited carbon surfaces or glass surfaces are representative of the types of surfaces for which the methods of the present invention are useful. The present inventive method is particularly useful in coating magnetic media such as computer drive hard disks. In the manufacture of computer disks, the surface may be a glass, or aluminum substrate with layers of magnetic media that is also coated by vapor deposition with a thin (10-50 Angstrom) layer of amorphous hydrogenated or nitrogenated carbon. The fluorolubricant may be deposited on the surface disk indirectly by applying the fluorolubricant to the carbon layer of the disk.

1,1,1,2,2,3,4,5,5,6,6,7,7,7-tetradecafluoroheptane, also known as HFC-63-14mcee, serves as solvent for the present inventive method and has CAS registry number [142347-09-9]. It may be prepared by methods described in U.S. Pat. Nos. 5,171,902, 5,723,701 and 6,506,950, herein incorporated by reference. HFC-63-14mcee can exist as several different stereoisomers. HFC-63-14mcee as used herein is meant to include all stereoisomers or mixtures thereof.

The present invention relates to a method for depositing fluorolubricant on a surface, said method comprising combining fluorolubricant with a solvent, that solvent being 1,1,1,2,2,3,4,5,5,6,6,7,7,7-tetradecafluoroheptane, contacting said combination of fluorolubricant and solvent with the surface and evaporating the solvent to form a fluorolubricant coating on the surface.

The first step of combining the fluorolubricant and solvent may be accomplished in any suitable manner, such as mixing in a suitable container, such as a beaker or other container that may be used as a bath for the deposition method. The fluorolubricant concentration in the solvent may be from about 0.010 percent (wt/wt) to about 0.50 percent (wt/wt).

The step of contacting said combination of fluorolubricant and solvent with the surface may be accomplished in any manner appropriate for said surface (considering the size and shape of the surface). A hard drive disk must be supported in some manner such as with a mandrel or some other support that may fit through the hole in the center of the disk. The disk will thus be held vertically such that the plane of the disk is perpendicular to the solvent bath. The mandrel may have different shapes including but not limited to, a cylindrical bar, or a V-shaped bar. The mandrel shape will determine the area of contact with the disk. The mandrel may be constructed of any material strong enough to hold the disk, including but not limited to metal, metal alloy, plastic or glass. Additionally, a disk may be supported vertically upright in a woven basket or be clamped into a vertical position with 1 or more clamps on the outer edge. The support may be constructed of any material with the strength to hold the disk, such as metal, metal alloy, plastic or glass. However the disk is supported, the disk will be lowered into a container holding a bath of the fluorolubricant/solvent combination. The bath may be held at room temperature or be heated or cooled to temperatures ranging from about 0° C. to about 50° C.

Alternatively, the disk may be supported as described above and the bath may be raised to immerse the disk. In either case, the disk may then be removed from the bath (either by lowering the bath or by raising the disk). Excess fluorolubricant/solvent combination can be drained into the bath.

Either of the methods for contacting the fluorolubricant/solvent combination with the disk surface of either lowering the disk into a bath or raising a bath to immerse the disk are commonly referred to as dip coating. Other means for contacting the disk with the fluorolubricant/solvent combination may be used in the present inventive method, including spraying or spin coating.

When the disk is removed from the bath, the disk will have a coating of fluorolubricant and some residual solvent (HFC-63-14mcee) on its surface. The residual solvent may be evaporated. Evaporation is usually performed at room temperature. However, other temperatures both above and below room temperature may be used as well for the evaporation step. Temperatures ranging from about 0° C. to about 100° C. may be used for evaporation. As the boiling point for HFC-63-14mcee, which is about 96° C., is higher than for the most commonly used solvents today, higher evaporation temperatures may be needed to prevent impractically long evaporation time.

The surface, or the disk if the surface is a disk, after completion of the coating method, will be left with a substantially uniform or uniform coating of fluorolubricant that is substantially free of solvent. The fluorolubricant may be applied to a thickness of less than about 300 nm, and alternately to a thickness of about 100 to about 300 nm.

HFC-63-14 is believed to be an improvement over the presently used solvents for deposition of fluorolubricant. Several solvents have been commonly used in the hard drive disk industry. These include PF-5060 (available from 3M™ Electronics Markets Materials Division, St. Paul, Minn., 55144, USA), Novec™ HFE-7100 (also available from 3M™), and Vertrel® XF (available from E. I. du Pont de Nemours & Co., Fluoroproducts, Wilmington, Del., 19898, USA). Vertrel® XF has been demonstrated to produce the most uniform fluorolubricant coatings due to its greater solvation of the fluorolubricant molecules. Not to be bound by theory, it is believed that the ability of a solvent to disrupt the intermolecular hydrogen bonds of the fluorolubricant is related to the solvent's ability to produce a uniform coating.

A uniform fluorolubricant coating is desired for proper functioning of a disk and thus areas of varying fluorolubricant thickness are undesirable on the surface of the disk. As more and more information is being stored on the same size disk, the read/write head must get closer and closer to the disk in order to function properly. If irregularities due to variation in coating thickness are present on the surface of the disk, the probability of contact of the head with these areas on the disk is much greater. While there is a desire to have enough fluorolubricant on the disk to flow into areas where it may be removed by head contact or other means, coating that is too thick may cause "smear," a problem associated with the read/write head picking up excess fluorolubricant.

One specific coating thickness irregularity observed in the industry is that known as the "rabbit ears" effect. These irregularities are visually detected on the surface of the disk after deposition of the fluorolubricant using the existing solvent systems. When the disk is contacted with the solution of fluorolubricant in solvent and then removed from the solution, any points where the solution may accumulate and not drain readily develop drops of solution. One such point of drop formation is the contact point (or points) with the mandrel or other support device with the disk. When a V-shaped mandrel is used, there are two contact points at which the mandrel contacts the inside edge of the disk. When solution of fluorolubricant forms drops in these locations an area of greater thickness of fluorolubricant is created when the solvent evaporates. The two points of contact with the disk produces what is known as a "rabbit ears" effect, because the areas of greater fluorolubricant thickness produce a pattern resembling rabbit ears visually detectable on the disk surface.

Vertrel® XF specialty fluid, comprising 1,1,1,2,3,4,4,5,5,5-decafluoropentane is used widely for producing overall uniform fluorolubricant coatings.

HFC-63-14mcee has the same advantages as Vertrel® XF in producing uniform fluorolubricant coatings, but is advantageous because it requires a lower concentration of fluorolubricant in the deposition fluorolubricant-solvent combination to produce the same fluorolubricant coating thickness. Therefore, HFC-63-14mcee is believed to reduce the problem of irregular fluorolubricant coating thickness. Not to be bound by theory, it is believed that the higher fluorine to hydrogen ratio on HFC-63-14mcee as compared to Vertrel® XF, will yield a lower affinity of the solvent for the carbon surface. If the solvent is not attracted to the surface, the fluorolubricant may more readily interact with the surface and become bonded there.

Lower concentrations of fluorolubricant in the lubricant-solvent combination means that the solution of lubricant-solvent that remains on the edges of the disk will contain less fluorolubricant. It is expect that the remaining solution in these areas will not have as great a negative effect on the coating thickness in those surface edges once the solvent has evaporated.

HFC-63-14mcee has other advantages over existing solvents used for deposition of fluorolubricant. The higher boiling point, about 96° C., will reduce evaporative loss of the solvent during use. Additionally, the high affinity for the fluorolubricant due to high fluorine to hydrogen ratio will provide improved solubility of fluorolubricants thus allowing use as a solvent for removing fluorolubricant from a surface.

When dip coating is used for depositing fluorolubricant on the surface, the pulling-up speed (speed at which the disk is removed from the bath), and the density of the fluorolubricant and the surface tension are relevant for determining the resulting film thickness of the fluorolubricant. Awareness of these parameters for obtaining the desired film thickness is required. Details on how these parameters effect coatings are given in, "Dip-Coating of Ultra-Thin Liquid Lubricant and its Control for Thin-Film Magnetic Hard Disks" in IEEE Transactions on Magnetics, vol. 31, no. 6, November 1995.

The present invention further relates to a method for cleaning surfaces by removing contaminants from the surface. The method for removing contaminants from a surface comprises contacting the surface having contaminants with solvent, that solvent comprising HFC-63-14mcee, to solubilize the contaminants, and recovering the surface from the solvent. The surface is then substantially free of contaminants.

In the present inventive method, the contacting may be accomplished by spraying, flushing, wiping with a substrate e.g., wiping cloth or paper, that has solvent incorporated in or on it, or by dipping or immersing the disk in a bath of solvent.

In the present inventive method, the recovering may be by removing the surface that has been contacted from the solvent bath (in a similar manner as described for the method for depositing a fluorolubricant on the surface or by allowing the solvent that has been sprayed, flushed or wiped on the disk to drain away). Additionally, any residual solvent that may be left behind after the completion of the previous steps may be evaporated in a manner similar to that for the deposition method as well.

The method for cleaning a surface may be applied to the same types of surfaces as the method for deposition as described previously. Semiconductor surfaces or magnetic media disks of silica, glass, metal or metal oxide, or carbon may have fluorolubricant removed by the method. In the method described above, contaminant may be removed from a disk by contacting the disk with the solvent and recovering the disk form the solvent.

Contaminants of the present invention refer to compounds that have been found to deposit on the carbon surface of a disk in the environment within which the carbon is deposited. Hydrocarbon based oils and greases and dioctylphthalate (DOP) are examples of the contaminants that may be found on the carbon-coated disks.

Additionally, the present invention relates to a method for solubilizing a fluorolubricant, said method comprising contacting HFC-63-14mcee with a fluorolubricant. HFC-63-14mcee may be demonstrated to have similar solvency to that of Vertrel® XF for fluorolubricants.

The present invention further relates to compositions comprising 1,1,1,2,2,3,4,5,5,6,6,7,7,7-tetradecafluoroheptane (HFC-63-14mcee), trans-1,2-dichloroethylene (trans-DCE) and at least one alcohol selected from the group consisting of methanol (MeOH), ethanol (EtOH) and isopropanol (IPA).

Trans-1,2-dichloroethylene, also known as trans-DCE, methanol, ethanol, and isopropanol are all available from commercially sources.

The azeotropic or azeotrope-like compositions of the present invention comprise:

from about 1 weight percent to about 40 weight percent HFC-63-14mcee, from about 55 weight percent to about 94 weight percent trans-DCE, and from about 1 weight percent to about 30 weight percent methanol; preferably, the compositions comprise from about 10 weight percent to about 30 weight percent HFC-63-14mcee, from about 60 weight percent to about 80 weight percent trans-DCE, and from about 3 weight percent to about 15 weight percent methanol;

from about 1 weight percent to about 40 weight percent HFC-63-14mcee, from about 55 weight percent to about 94 weight percent trans-DCE, and from about 1 weight percent to about 30 weight percent ethanol; preferably, the compositions comprise from about 10 weight percent to about 30 weight percent HFC-63-14mcee, from about 60 weight percent to about 80 weight percent trans-DCE, and from about 3 weight percent to about 15 weight percent ethanol; and from about 1 weight percent to about 40 weight percent HFC-63-14mcee, from about 55 weight percent to about 94 weight percent trans-DCE, and from about 1 weight percent to about 30 weight percent isopropanol; preferably, the compositions comprise from about 10 weight percent to about 30 weight percent HFC-63-14mcee, from about 60 weight percent to about 80 weight percent trans-DCE, and from about 3 weight percent to about 15 weight percent isopropanol.

The compositions of the present invention may be prepared by any convenient method to combine the desired amounts of the individual components. A preferred method is to weigh the desired component amounts and thereafter combine the components in an appropriate vessel. Agitation may be used, if desired.

An azeotropic composition is a constant boiling liquid admixture of two or more substances that behaves as a single substance, in that the vapor, produced by partial evaporation or distillation of the liquid has the same composition as the liquid, i.e., the admixture distills without substantial composition change. Constant boiling compositions, which are characterized as azeotropic, exhibit either a maximum or a minimum boiling point, as compared with that of the non-azeotropic mixtures of the same substances.

By "azeotrope-like composition," also referred to as "near azeotrope," is meant a constant boiling, or substantially constant boiling liquid admixture of two or more substances that behaves as a single substance. One way to characterize an azeotrope-like composition is that the vapor produced by partial evaporation or distillation of the liquid has substantially the same composition as the liquid from which it was evaporated or distilled. That is, the admixture distills/refluxes without substantial composition change. Another way to characterize an azeotrope-like composition is that the bubble point vapor pressure of the composition and the dew point vapor pressure of the composition at a particular temperature are substantially the same. Herein, a composition is azeotrope-like if, after 50 weight percent of the composition is removed such as by evaporation or boiling off, the difference in vapor pressure between the original composition and the composition remaining after 50 weight percent of the original composition has been removed by evaporation or boil off is less than about 10 percent.

In cleaning apparati, including vapor degreasing and vapor defluxing equipment, compositions may be lost during operation through leaks in shaft seals, hose connections, soldered joints and broken lines. In addition, the working composition may be released to the atmosphere during maintenance procedures on equipment. If the composition is not a pure component or azeotropic or azeotrope-like composition, the composition may change when leaked or discharged to the atmosphere from the equipment, which may cause the composition remaining in the equipment to exhibit unacceptable performance. Accordingly, it is desirable to use as a cleaning composition a single fluorinated hydrocarbon or an azeotropic or azeotrope-like composition that fractionates to a negligible degree upon leak or boil off.

Vapor degreasing or vapor defluxing apparatus function in some aspects similarly to a distillation column. These apparatus have one or more chambers for rinsing with a composition and one or more chambers for boiling with a composition. As such, if a composition that is a non-azeotropic mixture were to be used in such an apparatus, the composition would fractionate and the performance in removing residue would be altered. Further, it would not be possible to recover, clean up and re-use the composition as the composition would be changed from that of the original. Therefore, the use of azeotropic or azeotrope-like compositions in these types of apparatus is highly recommended and makes possible recovery and recycle of the compositions used therein.

The azeotropic compositions of the present invention are listed in Table 1.

TABLE 1

| Components | Azeotrope Point (wt %) | Temp (° C.) |
|---|---|---|
| HFC-63-14mcee/trans-DCE/MeOH | 18.7/73.2/8.1 | 40 |
| HFC-63-14mcee/trans-DCE/EtOH | 21.8/73.8/4.4 | 45 |
| HFC-63-14mcee/trans-DCE/IPA | 22.5/75.0/2.5 | 45 |

The present inventive azeotropic compositions are effective cleaning agents, defluxers and degreasers. In particular, the present inventive azeotropic compositions are useful when defluxing circuit boards with components such as Flip chip, μBGA (ball grid array), and Chip scale or other advanced high-density packaging components. Flip chips, μBGA, and Chip scale are terms that describe high density packaging components used in the semi-conductor industry and well understood by those working in the field.

In a preferred embodiment the present invention relates to a process for removing residue from a surface or substrate, comprising: contacting the surface or substrate with a composition of the present invention and recovering the surface or substrate from the composition.

In the inventive process, the surface or substrate may be an integrated circuit device, in which case, the residue comprises soldering flux or oil. The integrated circuit device may be a circuit board with various types of components, such as Flip chips, μBGAs, or Chip scale packaging components. Different types of oil residues may be mineral oils, motor oils, or silicone oils. The means for contacting the surface is not critical and may be accomplished by immersion of the device in a bath containing the composition, spraying the device with the composition or wiping the device with a substrate that has been wet with the composition. Alternatively, the composition may also be used in a vapor degreasing apparatus designed for such residue removal. Such vapor degreasing equipment is available from suppliers such as Forward Technology (a subsidiary of the Crest Group, Trenton, N.J.), Trek Industries (Azusa, Calif.), and Ultronix, Inc. (Hatfield, Pa.) among others.

An effective composition for removing residue from a surface would be one that had a Kauri-Butanol value (Kb) of at least about 25, preferably about 100. The Kauri-Butanol value (Kb) for a given composition reflects the ability of said composition to solubilize various organic residues (e.g., machine and conventional oils, flux residues, and greases or lubricants). The Kb value may be determined by ASTM D-1133-94.

The present invention further relates to compositions comprising 1,1,1,2,2,3,4,5,5,6,6,7,7,7-tetradecafluoroheptane (HFC-63-14mcee) and at least one other compound selected from the group consisting of alcohols, amines, esters, fluoroethers, halocarbons, hydrocarbons, ketones, nitriles, 2,2-dimethyl-1,3-dioxolane, 1,2-dimethoxyethane and nitromethane.

Table 2 lists compounds with which HFC-63-14mcee may be combined in order to form the present inventive compositions.

TABLE 2

| Name | Chemical formula | Synonym (or abbreviation) |
|---|---|---|
| Hydrocarbons | | |
| cyclohexane | cyclo —$CH_2CH_2CH_2CH_2CH_2CH_2$— | |
| 2,2,3-trimethylbutane | $(CH_3)_2CHC(CH_3)_3$ | |
| 2,4-dimethylpentane | $(CH_3)_2CHCH_2CH(CH_3)_2$ | |
| 3,3-dimethylpentane | $CH_3CH_2C(CH_3)_2CH_2CH_3$ | |
| 2,3-dimethylpentane | $CH_3CH_2CH(CH_3)CH(CH_3)_2$ | |
| 2-methylhexane | $CH_3(CH_2)_3CH(CH_3)_2$ | |
| 3-methylhexane | $CH_3(CH_2)_2CH(CH_3)CH_2CH_3$ | |
| n-heptane | $CH_3(CH_2)_5CH_3$ | |
| methylcyclohexane | cyclo —$CH_2(CH_3)CH_2(CH_2)_3CH_2$— | |
| toluene | $C_6H_5CH_3$ | |
| isooctane | $(CH_3)_2CHCH_2C(CH_3)_3$ | |
| n-octane | $CH_3(CH_2)_6CH_3$ | |
| Halocarbons | | |
| 2-bromopropane | $CH_3CHBrCH_3$ | 2-BP |
| 1-bromopropane | $CH_2BrCH_2CH_3$ | 1-BP |
| 1,2-dichloroethane | $CH_2ClCH_2Cl$ | |
| 1,1-dichloroethane | $CHCl_2CH_3$ | |
| fluorobenzene | $C_6H_5F$ | |
| methylene bromide | $CH_2Br_2$ | |
| trichloroethylene | $CHCl=CCl_2$ | TCE |
| tetrachloroethylene (or perchloroethylene) | $CCl_2=CCl_2$ | PCE |
| chlorobenzene | $C_6H_5Cl$ | |
| trans-1,2-dichloroethylene | $CHCl=CHCl$ | trans-DCE |
| cis-1,2-dichloroethylene | $CHCl=CHCl$ | cis-DCE |
| Alcohols | | |
| methanol | $CH_3OH$ | MeOH |
| ethanol | $CH_3CH_2OH$ | EtOH |
| n-propanol | $CH_3CH_2CH_2OH$ | n-PrOH |
| Isopropanol | $CH_3CH(OH)CH_3$ | IPA |
| 2-methyl-2-propanol | $CH_3CH(CH_3)CH_2OH$ | |
| 2-methyl-2-butanol | $CH_3CH_2CH(CH_3)CH_2OH$ | |
| 2-butanol (or sec-butanol) | $CH_3CH(OH)CH_2CH_3$ | sec-BuOH |
| 2-methyl-1-propanol (or isobutanol) | $CH_3CH(CH_3)CH_2OH$ | Iso-BuOH |
| n-butanol | $CH_3(CH_2)_3OH$ | n-BuOH |
| 2-methoxyethanol | $CH_2OHCH_2OCH_3$ | |
| 2,2,3,3,3-pentafluoro-1-propanol | $CH_2(OH)CF_2CF_3$ | |
| 2,2,3,3-tetrafluoro-1-propanol | $CH_2(OH)CF_2CHF_2$ | |
| 1,1,1,3,3,3-hexafluoro-2-propanol | $CF_3CH(OH)CF_3$ | |
| 2,2,2-trifluoroethanol | $CH_2OHCF_3$ | |
| Nitriles | | |
| Acetonitrile | $CH_3CN$ | |
| Propionitrile | $CH_3CH_2CN$ | |
| Butyronitrile | $CH_3CH_2CH_2CN$ | |
| Amines | | |
| n-methylmorpholine | Cyclo —$OCH_2CH_2N(CH_3)CH_2CH_2$— | |
| Morpholine | cyclo —$OCH_2CH_2NH(CH_2)_2$— | |
| Esters | | |
| ethyl acetate | $CH_3C(O)OCH_2CH_3$ | |
| methyl propionate | $CH_3CH_2C(O)OCH_3$ | |
| n-propyl formate | $HC(O)OCH_2CH_2CH_3$ | |
| Dimethyl carbonate | $(CH_3O)_2CO$ | |
| Isopropyl acetate | $CH_3C(O)OCH(CH_3)_2$ | |
| isobutyl formate | $HC(O)OCH_2CH(CH_3)_2$ | |
| ethyl propionate | $CH_3CH_2C(O)OCH_2CH_3$ | |
| n-propyl acetate | $CH_3C(O)OCH_2CH_2CH_3$ | |
| methyl n-butyrate | $CH_3CH_2CH_2C(O)OCH_3$ | |
| butyl formate | $HC(O)O(CH_2)_3CH_3$ | |
| diethyl carbonate | $(CH_3CH_2O)_2CO$ | |
| Ketones | | |
| 2-butanone (or methyl ethyl ketone) | $CH_3C(O)CH_2CH_3$ | MEK |
| 3-methyl-2-butanone (or methyl isopropyl ketone) | $CH_3C(O)CH(CH_3)_2$ | MIPK |
| 2-bromo-1,1,1,4,4,5,5,5-octafluoro-2-(trifluoromethyl)-3-pentanone | $(CF_3)_2CBrC(O)CF_2CF_3$ | |
| Others | | |
| mixture of isomers-1,1,1,2,2,3,3,4,4-nonafluoro-4-methoxybutane and 2-(methoxy-difluoromethyl)-1,1,1,2,3,3,3-heptafluoropropane | $CF_3CF_2CF_2CF_2OCH_3$ and $(CF_3)_2CFCF_2OCH_3$ | $C_4F_9OCH_3$ |
| mixture of isomers-1-ethoxy-1,1,2,2,3,3,4,4,4-nonafluorobutane and 2-(ethoxy-difluoromethyl)-1,1,1,2,3,3,3-heptafluoropropane | $CF_3CF_2CF_2CF_2OC_2H_5$ and $(CF_3)_2CFCF_2OC_2H_5$ | $C_4F_9OC_2H_5$ |
| 1,1,1,2,2,3,4,5,5,5-decafluoro-3-methoxy-4-(trifluoromethyl)-pentane | $CF_3CF_2CF(OCH_3)CF(CF_3)CF_3$ | DMTP |
| 2,2-dimethyl-1,3-dioxolane | cyclo —$OC(CH_3)_2OCH_2CH_2$— | |
| 1,2-dimethoxyethane | $CH_3OCH_2CH_2OCH_3$ | |
| Nitromethane | $CH_3NO_2$ | |

The compounds listed in Table 2 may be readily prepared by those skilled in the art and are also commercially available from chemical supply houses. 1,1,1,2,2,3,4,5,5,5-decafluoro-3-methoxy-4-(trifluoromethyl)-pentane, $C_4F_9OCH_3$, and $C_4F_9OC_2H_5$ are available from 3M™ (St. Paul, Minn.).

These azeotropic or azeotrope-like compositions of the present invention may be prepared by any convenient method by combining the desired amounts of the individual components. A preferred method is to weigh the desired component amounts and thereafter combining the components in an appropriate vessel. Agitation may be used, if desired.

The azeotropic compositions of the present invention are listed in Table 3.

TABLE 3

| | Component | Azeotrope point | | Azeotrope |
|---|---|---|---|---|
| HFC-63-14mcee plus (B) | B Boiling point (° C.) | wt % HFC-63-14mcee | wt % (B) | Boiling Point (° C.) |
| Hydrocarbons | | | | |
| cyclohexane | 80.7 | 61.1 | 38.9 | 71.5 |
| 2,2,3-trimethylbutane | 80.9 | 60.8 | 39.2 | 69.5 |

TABLE 3-continued

| HFC-63-14mcee plus (B) | B Boiling point (° C.) | Azeotrope point wt % HFC-63-14mcee | wt % (B) | Azeotrope Boiling Point (° C.) |
|---|---|---|---|---|
| 2,4-dimethylpentane | 80.5 | 60.6 | 39.4 | 69.4 |
| 3,3-dimethylpentane | 86.1 | 65.1 | 34.9 | 72.8 |
| 2,3-dimethylpentane | 89.8 | 68.4 | 31.6 | 75.4 |
| 2-methylhexane | 90.1 | 68.3 | 31.7 | 75.4 |
| 3-methylhexane | 91.9 | 69.6 | 30.4 | 76.4 |
| n-heptane | 98.4 | 74.9 | 25.1 | 80.5 |
| methylcyclohexane | 98.2 | 73.2 | 26.8 | 80.4 |
| toluene | 110.6 | 83.8 | 16.2 | 87.2 |
| isooctane | 99.2 | 72.9 | 27.1 | 78.9 |
| n-octane | 98.2 | 88.4 | 11.6 | 90.0 |
| Halocarbons | | | | |
| 2-bromopropane | 59.4 | 33.6 | 66.4 | 56.8 |
| 1-bromopropane | 71.0 | 46.0 | 54.0 | 66.3 |
| 1,2-dichloroethane | 83.5 | 59.4 | 40.6 | 74.5 |
| 1,1-dichloroethane | 57.0 | 20.7 | 79.3 | 56.4 |
| fluorobenzene | 84.7 | 64.6 | 35.4 | 75.1 |
| methylene bromide | 97.0 | 64.9 | 35.1 | 86.0 |
| trichloroethylene | 87.5 | 59.7 | 40.3 | 77.0 |
| tetrachloroethylene | 121.2 | 82.6 | 17.4 | 91.4 |
| chlorobenzene | 132.0 | 93.6 | 6.4 | 94.1 |
| trans-1,2-dichloroethylene | 48.0 | 24.0 | 76.0 | 45.0 |
| cis-1,2-dichloroethylene | 60.5 | 37.0 | 63.0 | 58.2 |
| Alcohols | | | | |
| methanol | 65.6 | 47.0 | 53.0 | 65.5 |
| ethanol | 78.3 | 79.4 | 20.6 | 71.3 |
| n-propanol | 97.2 | 86.5 | 13.5 | 82.3 |
| Isopropanol | 82.3 | 77.9 | 22.1 | 73.5 |
| 2-methyl-2-propanol | 82.2 | 73.3 | 26.7 | 71.8 |
| 2-methyl-2-butanol | 102.0 | 82.9 | 17.1 | 82.1 |
| 2-butanol | 98.0 | 83.3 | 16.7 | 81.0 |
| Isobutanol | 107.7 | 87.8 | 12.2 | 85.5 |
| n-butanol | 117.7 | 91.7 | 8.3 | 89.4 |
| 2-methoxyethanol | 124.6 | 93.4 | 6.6 | 89.0 |
| 2,2,3,3,3-pentafluoro-1-propanol | 81.8 | 57.0 | 43.0 | 76.9 |
| 2,2,3,3-tetrafluoro-1-propanol | 109.0 | 87.4 | 12.6 | 92.2 |
| 1,1,1,3,3,3-hexafluoro-2-propanol | 59.0 | 14.5 | 85.5 | 58.7 |
| 2,2,2-trifluoroethanol | 78.4 | 62.0 | 38.0 | 73.3 |
| Nitriles | | | | |
| acetonitrile | 81.5 | 73.6 | 26.4 | 75.1 |
| propionitrile | 97.4 | 83.0 | 17.0 | 83.9 |
| butyronitrile | 116.0 | 90.9 | 9.1 | 91.2 |
| Amines | | | | |
| n-methylmorpholine | 115.0 | 86.3 | 13.7 | 89.6 |
| morpholine | 128.9 | 95.6 | 4.4 | 94.5 |
| Esters | | | | |
| ethyl acetate | 72.1 | 60.6 | 39.4 | 70.3 |
| methyl propionate | 87.7 | 61.6 | 38.4 | 71.2 |
| n-propyl formate | 80.8 | 64.0 | 36.0 | 72.9 |
| dimethyl carbonate | 90.5 | 71.1 | 28.9 | 79.7 |
| Isopropyl acetate | 88.2 | 68.3 | 31.7 | 76.9 |
| Isobutyl formate | 98.4 | 76.5 | 23.5 | 82.9 |
| ethyl propionate | 99.1 | 76.6 | 23.4 | 83.0 |
| n-propyl acetate | 101.5 | 78.3 | 21.7 | 84.2 |
| methyl n-butyrate | 102.6 | 79.0 | 21.0 | 84.7 |
| butyl formate | 106.6 | 82.2 | 17.8 | 86.9 |
| diethyl carbonate | 126.8 | 91.5 | 8.5 | 93.1 |
| Ketones | | | | |
| 2-butanone | 79.6 | 94.5 | 5.5 | 96.0 |
| 3-methyl-2-butanone | 94.5 | 78.0 | 22.0 | 99.9 |
| $(CF_3)_2CBrC(O)CF_2CF_3$ | 96.5 | 64.6 | 35.4 | 94.1 |
| Fluoroethers | | | | |
| DMTP | 96.6 | 6.2 | 93.8 | 90.0 |
| Other | | | | |
| 2,2-dimethyl-1,3-dioxolane | 92.5 | 72.2 | 27.8 | 76.2 |
| 1,2-dimethoxyethane | 83.5 | 67.6 | 36.4 | 71.6 |
| nitromethane | 101.2 | 81.0 | 19.0 | 90.0 |

Additionally, the azeotropic compositions of the present invention may include ternary and quaternary azeotropic compositions comprising compounds from Table 2. Two of these higher order azeotropic compositions are exemplified in Table 4 along with the atmospheric pressure boiling points for the compositions.

TABLE 4

| Composition | Azeotrope point Concentrations (wt %) | Azeotrope Boiling Point (° C.) |
|---|---|---|
| HFC-63-14mcee/$C_4F_9OC_2H_5$/trans-DCE | 12.1/16.8/71.1 | 50 |
| HFC-63-14mcee/$C_4F_9OC_2H_5$/trans-DCE/MeOH | 7.8/16.4/67.9/7.9 | 40-43 |

The azeotrope-like compositions of the present invention are listed in Table 5.

TABLE 5

| Composition | Azeotrope-Like Ranges wt % HFC-63-14mcee/wt % (B) |
|---|---|
| HFC-63-14mcee plus B: | |
| Hydrocarbons | |
| Cyclohexane | 38-83/62-17 |
| 2,2,3-trimethylbutane | 39-82/61-18 |
| 2,4-dimethylpentane | 39-82/61-18 |
| 3,3-dimethylpentane | 42-84/58-16 |
| 2,3-dimethylpentane | 45-86/55-14 |
| 2-methylhexane | 45-86/55-14 |
| 3-methylhexane | 46-86/54-14 |
| n-heptane | 51-89/49-11 |
| Methylcyclohexane | 48-89/52-11 |
| Toluene | 59-99/41-1 |
| Isooctane | 49-88/51-12 |
| n-octane | 62-99/38-1 |
| Halocarbons | |
| 2-bromopropane | 1-68/99-32 |
| 1-bromopropane | 19-74/81-26 |
| 1,2-dichloroethane | 36-82/64-18 |
| 1,1-dichloroethane | 1-62/99-38 |
| Fluorobenzene | 39-85/61-15 |
| Methylene bromide | 36-99/64-1 |
| Trichloroethylene | 35-80/65-20 |
| Tetrachloroethylene | 53-99/47-1 |
| Chlorobenzene | 70-99/30-1 |
| trans-1,2-chloroethylene | 1-68/99-32 |
| cis-1,2-dichloroethylene | 1-72/99-28 |
| Alcohols | |

TABLE 5-continued

| Composition | Azeotrope-Like Ranges wt % HFC-63-14mcee/wt % (B) |
|---|---|
| Methanol | 1-93/99-7 |
| Ethanol | 58-92/42-1 |
| n-propanol | 69-94/31-6 |
| Isopropanol | 58-91/42-9 |
| 2-methyl-2-propanol | 52-88/48-12 |
| 2-methyl-2-butanol | 63-92/37-8 |
| 2-butanol | 64-93/36-7 |
| Isobutanol | 70-95/30-5 |
| n-butanol | 75-99/25-1 |
| 2-methoxyethanol | 77-97/23-3 |
| 2,2,2-trifluoroethanol | 1-84/99-16 |
| 2,2,3,3,3-pentafluoro-1-propanol | 1-82/99-18 |
| 2,2,3,3-tetrafluoro-1-propanol | 59-99/41-1 |
| 1,1,1,3,3,3-hexafluoro-2-propanol | 1-64/99-36 |
| Nitriles | |
| Acetonitrile | 46-91/54-9 |
| Propionitrile | 61-96/39-4 |
| Butyronitrile | 71-99/29-1 |
| Amines | |
| n-methylmorpholine | 64-99/36-1 |
| Morpholine | 74-99/26-1 |
| Esters | |
| ethyl acetate | 34-83/66-17 |
| methyl propionate | 35-83/65-17 |
| n-propyl formate | 38-84/62-16 |
| dimethyl carbonate | 46-89/54-11 |
| isopropyl acetate | 44-86/56-14 |
| isobutyl formate | 53-91/47-9 |
| ethyl propionate | 53-91/47-9 |
| n-propyl acetate | 55-92/45-8 |
| methyl n-butyrate | 56-93/44-7 |
| butyl formate | 59-99/41-1 |
| diethyl carbonate | 68-99/32-1 |
| Ketones | |
| 2-butanone | 1-99/99-1 |
| 3-methyl-2-butanone | 1-99/99-1 |
| $(CF_3)_2CBrC(O)CF_2CF_3$ | 1-99/99-1 |
| Fluoroethers | |
| DMTP | 1-99/99-1 |
| Other | |
| Nitromethane | 47-99/53-1 |
| 1,2-dimethoxyethane | 45-85/55-15 |
| 2,2-dimethyl-1,3-dioxolane | 50-87/50-13 |

In addition to the binary azeotrope-like compositions in the preceding table, higher order (ternary or quaternary) azeotrope-like compositions are included in the present invention. Examples of ternary or higher order azeotrope-like compositions are given in Table 6.

TABLE 6

| Composition | Azeotrope-like Range (Wt %) | Preferred Range (Wt %) |
|---|---|---|
| HFC-63-14mcee/$C_4F_9OCH_3$/trans-DCE | 1-68/1-98/1-98 | 1-60/1-84/15-98 |
| HFC-63-14mcee/$C_4F_9OC_2H_5$/trans-DCE | 1-68/1-71/28-98 | 1-60/1-50/40-80 |
| HFC-63-14mcee/$C_4F_9OC_2H_5$/trans-DCE/methanol | 1-68/1-71/28-98/1-30 | 1-60/1-50/40-80/1-30 |

Any of the compositions of the present invention may further comprise an aerosol propellant. Aerosol propellants may assist in delivering the present compositions from a storage container to a surface in the form of an aerosol. Aerosol propellant is optionally included in the present compositions in up to 25 weight percent of the total composition. Representative aerosol propellants comprise air, nitrogen, carbon dioxide, dimethyl ether (DME, $CH_3OCH_3$), difluoromethane (HFC-32, $CH_2F_2$), trifluoromethane (HFC-23, $CHF_3$), difluoroethane (HFC-152a, $CHF_2CH_3$), trifluoroethane (HFC-143a, $CH_3CF_3$; or HFC-143, $CHF_2CH_2F$), tetrafluoroethane (HFC-134a, $CF_3CH_2F$; HFC-134, $CHF_2CHF_2$), pentafluoroethane (HFC-125, $CF_3CHF_2$), heptafluoropropane (HFC-227ea, $CF_3CHFCF_3$), pentafluoropropane (HFC-245fa, $CF_3CH_2CHF_2$), hydrocarbons, including propane, n-butane, isobutane, n-pentane, cyclopentane, 2-methylbutane, among others, and any combinations of those compounds in the list.

The present invention further relates to refrigerant or heat transfer fluid compositions comprising 1,1,1,2,2,3,4,5,5,6,6,7,7,7-tetradecafluoroheptane (HFC-63-14mcee) and at least one hydrocarbon, halocarbon, alcohol, ester, 2,2-dimethyl-1,3-dioxolane, or acetonitrile. Representative hydrocarbons, halocarbons, alcohols, esters etc., are listed in Table 2.

The preferred refrigerant or heat transfer fluid compositions of the present invention include HFC-63-14mcee with at least one compound selected from the group consisting of:
cyclohexane;
2,2,3-trimethylbutane;
2,4-dimethylpentane;
3,3-dimethylpentane;
2,3-dimethylpentane
2-methylhexane;
3-methylhexane,
isooctane;
2-bromopropane;
1-bromopropane;
1,2-dichloroethane;
1,1-dichloroethane;
fluorobenzene;
o-difluorobenzene;
m-difluorobenzene;
p-difluorobenzene;
trichloroethylene;
methanol;
ethanol;
2-methyl-2-propanol;
2,2-dimethyl-1,3-dioxolane;
acetonitrile;
ethyl acetate;
methyl propionate;
n-propyl formate;
dimethylcarbonate;
isopropyl acetate;
2,2,2-trifluoroethanol;
isopropanol;
2,2,3,3,3-pentafluoro-1-propanol;
2,2,3,3-tetrafluoro-1-propanol; and
1,1,1,3,3,3-hexafluoro-2-propanol.

The refrigerant or heat transfer fluid compositions of the present invention may additionally be azeotropic or azeotrope-like compositions as listed in Table 3, Table 4, Table 5 and Table 6.

The refrigerant or heat transfer fluid compositions of the present invention may further comprise about 0.01 weight percent to about weight percent of a stabilizer, free radical scavenger or antioxidant. Such additives include but are not limited to, nitromethane, hindered phenols, hydroxylamines, thiols, phosphites, or lactones. Single additives or combinations may be used.

The refrigerant or heat transfer fluid compositions of the present invention may further comprise about 0.01 weight percent to about 5 weight percent of a water scavenger (drying compound). Such water scavengers may comprise ortho esters such as trimethyl-, triethyl-, or tripropylorthoformate.

The refrigerant or heat transfer fluid compositions of the present invention may further comprise an ultra-violet (UV) dye and optionally a solubilizing agent. The UV dye is a useful component for detecting leaks of the refrigerant and heat transfer fluid compositions by permitting one to observe the fluorescence of the dye in the refrigerant or heat transfer fluid compositions at a leak point or in the vicinity of refrigeration or air-conditioning apparatus. One may observe the fluorescence of the dye under an ultra-violet light. Solubilizing agents may be needed to increase solubility of such UV dyes in some refrigerants and heat transfer fluids.

By "ultra-violet" dye is meant a UV fluorescent composition that absorbs light in the ultra-violet or "near" ultra-violet region of the electromagnetic spectrum. The fluorescence produced by the UV fluorescent dye under illumination by a UV light that emits radiation with wavelength anywhere from 10 nanometer to 750 nanometer may be detected. Therefore, if refrigerant or heat transfer fluid containing such a UV fluorescent dye is leaking from a given point in a refrigeration or air-conditioning apparatus, the fluorescence can be detected at the leak point. Such UV fluorescent dyes include but are not limited to naphthalimides, perylenes, coumarins, anthracenes, phenanthracenes, xanthenes, thioxanthenes, naphthoxanthenes, fluoresceins, and derivatives or combinations thereof. Solubilizing agents of the present invention comprise at least one compound selected from the group consisting of hydrocarbons, hydrocarbon ethers, polyoxyalkylene glycol ethers, amides, nitriles, ketones, chlorocarbons, esters, lactones, aryl ethers, fluoroethers and 1,1,1-trifluoroalkanes.

Hydrocarbon solubilizing agents of the present invention comprise hydrocarbons including straight chained, branched chain or cyclic alkanes or alkenes containing 5 or fewer carbon atoms and only hydrogen with no other functional groups. Representative hydrocarbon solubilizing agents comprise propane, propylene, cyclopropane, n-butane, isobutane, and n-pentane. It should be noted that if the refrigerant is a hydrocarbon, then the solubilizing agent may not be the same hydrocarbon.

Hydrocarbon ether solubilizing agents of the present invention comprise ethers containing only carbon, hydrogen and oxygen, such as dimethyl ether (DME).

Polyoxyalkylene glycol ether solubilizing agents of the present invention are represented by the formula

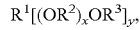

wherein x is an integer from 1-3; y is an integer from 1-4; $R^1$ is selected from hydrogen and aliphatic hydrocarbon radicals having 1 to 6 carbon atoms and y bonding sites; $R^2$ is selected from aliphatic hydrocarbylene radicals having from 2 to 4 carbon atoms; $R^3$ is selected from hydrogen, and aliphatic and alicyclic hydrocarbon radicals having 1 to 6 carbon atoms; at least one of $R^1$ and $R^3$ is selected from said hydrocarbon radical; and wherein said polyoxyalkylene glycol ethers have a molecular weight of from about 100 to about 300 atomic mass units. As used herein, bonding sites mean radical sites available to form covalent bonds with other radicals. Hydrocarbylene radicals mean divalent hydrocarbon radicals.

In the present invention, preferable polyoxyalkylene glycol ether solubilizing agents are represented by $R^1[(OR^2)_x OR^3]_y$, wherein x is preferably 1-2; y is preferably 1; $R^1$ and $R^3$ are preferably independently selected from hydrogen and aliphatic hydrocarbon radicals having 1 to 4 carbon atoms; $R^2$ is preferably selected from aliphatic hydrocarbylene radicals having from 2 or 3 carbon atoms, most preferably 3 carbon atoms; the polyoxyalkylene glycol ether molecular weight is preferably from about 100 to about 250 atomic mass units, most preferably from about 125 to about 250 atomic mass units. The $R^1$ and $R^3$ hydrocarbon radicals having 1 to 6 carbon atoms may be linear, branched or cyclic. Representative $R^1$ and $R^3$ hydrocarbon radicals include methyl, ethyl, propyl, isopropyl, butyl, isobutyl, sec-butyl, tert-butyl, pentyl, isopentyl, neopentyl, tert-pentyl, cyclopentyl, and cyclohexyl. Where free hydroxyl radicals on the present polyoxyalkylene glycol ether solubilizing agents may be incompatible with certain compression refrigeration apparatus materials of construction (e.g. Mylar®), $R^1$ and $R^3$ are preferably aliphatic hydrocarbon radicals having 1 to 4 carbon atoms, most preferably 1 carbon atom. The $R^2$ aliphatic hydrocarbylene radicals having from 2 to 4 carbon atoms form repeating oxyalkylene radicals —$(OR^2)_x$— that include oxyethylene radicals, oxypropylene radicals, and oxybutylene radicals. The oxyalkylene radical comprising $R^2$ in one polyoxyalkylene glycol ether solubilizing agent molecule may be the same, or one molecule may contain different $R^2$ oxyalkylene groups. The present polyoxyalkylene glycol ether solubilizing agents preferably comprise at least one oxypropylene radical. Where $R^1$ is an aliphatic or alicyclic hydrocarbon radical having 1 to 6 carbon atoms and y bonding sites, the radical may be linear, branched or cyclic. Representative $R^1$ aliphatic hydrocarbon radicals having two bonding sites include, for example, an ethylene radical, a propylene radical, a butylene radical, a pentylene radical, a hexylene radical, a cyclopentylene radical and a cyclohexylene radical. Representative $R^1$ aliphatic hydrocarbon radicals having three or four bonding sites include residues derived from polyalcohols, such as trimethylolpropane, glycerin, pentaerythritol, 1,2,3-trihydroxycyclohexane and 1,3,5-trihydroxycyclohexane, by removing their hydroxyl radicals.

Representative polyoxyalkylene glycol ether solubilizing agents include but are not limited to: $CH_3OCH_2CH(CH_3)O(H$ or $CH_3)$ (propylene glycol methyl (or dimethyl)ether), $CH_3O[CH_2CH(CH_3)O]_2(H$ or $CH_3)$ (dipropylene glycol methyl (or dimethyl)ether), $CH_3O[CH_2CH(CH_3)O]_3(H$ or $CH_3)$ (tripropylene glycol methyl (or dimethyl)ether), $C_2H_5OCH_2CH(CH_3)O(H$ or $C_2H_5)$ (propylene glycol ethyl (or diethyl)ether), $C_2H_5O[CH_2CH(CH_3)O]_2(H$ or $C_2H_5)$ (dipropylene glycol ethyl (or diethyl)ether), $C_2H_5O[CH_2CH(CH_3)O]_3(H$ or $C_2H_5)$ (tripropylene glycol ethyl (or diethyl) ether), $C_3H_7OCH_2CH(CH_3)O(H$ or $C_3H_7)$ (propylene glycol n-propyl (or di-n-propyl)ether), $C_3H_7O[CH_2CH(CH_3)O]_2(H$ or $C_3H_7)$ (dipropylene glycol n-propyl (or di-n-propyl)ether), $C_3H_7O[CH_2CH(CH_3)O]_3(H$ or $C_3H_7)$ (tripropylene glycol n-propyl (or di-n-propyl)ether), $C_4H_9OCH_2CH(CH_3)OH$ (propylene glycol n-butyl ether), $C_4H_9O[CH_2CH(CH_3)O]_2(H$ or $C_4H_9)$ (dipropylene glycol n-butyl (or di-n-butyl) ether), $C_4H_9O[CH_2CH(CH_3)O]_3(H$ or $C_4H_9)$ (tripropylene glycol n-butyl (or di-n-butyl) ether), $(CH_3)_3COCH_2CH(CH_3)OH$ (propylene glycol t-butyl ether), $(CH_3)_3CO[CH_2CH(CH_3)O]_2(H$ or $(CH_3)_3)$ (dipropylene glycol t-butyl (or di-t-butyl)ether), $(CH_3)_3CO[CH_2CH(CH_3)O]_3(H$ or $(CH_3)_3)$ (tripropylene glycol t-butyl (or di-t-butyl) ether), C$_5$H$_{11}$OCH$_2$CH(CH$_3$)OH (propylene glycol n-pentyl ether), C$_4$H$_9$OCH$_2$CH(C$_2$H$_5$)OH (butylene glycol n-butyl ether), C$_4$H$_9$O[CH$_2$CH(C$_2$H$_5$)O]$_2$H (dibutylene glycol n-butyl ether), trimethylolpropane tri-n-butyl ether (C$_2$H$_5$C(CH$_2$O (CH$_2$)$_3$CH$_3$)$_3$) and trimethylolpropane di-n-butyl ether (C$_2$H$_5$C(CH$_2$OC(CH$_2$)$_3$CH$_3$)$_2$CH$_2$OH).

Amide solubilizing agents of the present invention comprise those represented by the formulae R$^1$C(O)NR$^2$R$^3$ and cyclo-[R$^4$C(O)N(R$^5$)-], wherein R$^1$, R$^2$, R$^3$ and R$^5$ are independently selected from aliphatic and alicyclic hydrocarbon radicals having from 1 to 12 carbon atoms; R$^4$ is selected from aliphatic hydrocarbylene radicals having from 3 to 12 carbon atoms; and wherein said amides have a molecular weight of from about 100 to about 300 atomic mass units. The molecular weight of said amides is preferably from about 160 to about 250 atomic mass units. R$^1$, R$^2$, R$^3$ and R$^5$ may optionally include substituted hydrocarbon radicals, that is, radicals containing non-hydrocarbon substituents selected from halogens (e.g., fluorine, chlorine) and alkoxides (e.g. methoxy). R$^1$, R$^2$, R$^3$ and R$^5$ may optionally include heteroatom-substituted hydrocarbon radicals, that is, radicals, which contain the atoms nitrogen (aza-), oxygen (oxa-) or sulfur (thia-) in a radical chain otherwise composed of carbon atoms. In general, no more than three non-hydrocarbon substituents and heteroatoms, and preferably no more than one, will be present for each 10 carbon atoms in R$^{1-3}$, and the presence of any such non-hydrocarbon substituents and heteroatoms must be considered in applying the aforementioned molecular weight limitations. Preferred amide solubilizing agents consist of carbon, hydrogen, nitrogen and oxygen. Representative R$^1$, R$^2$, R$^3$ and R$^5$ aliphatic and alicyclic hydrocarbon radicals include methyl, ethyl, propyl, isopropyl, butyl, isobutyl, sec-butyl, tert-butyl, pentyl, isopentyl, neopentyl, tert-pentyl, cyclopentyl, cyclohexyl, heptyl, octyl, nonyl, decyl, undecyl, dodecyl and their configurational isomers. A preferred embodiment of amide solubilizing agents are those wherein R$^4$ in the aforementioned formula cyclo-[R$^4$C(O)N(R$^5$)—] may be represented by the hydrocarbylene radical (CR$^6$R$^7$)$_n$, in other words, the formula cyclo-[(CR$^6$R$^7$)$_n$C(O)N(R$^5$)—] wherein the previously-stated values for molecular weight apply; n is an integer from 3 to 5; R$^5$ is a saturated hydrocarbon radical containing 1 to 12 carbon atoms; R$^6$ and R$^7$ are independently selected (for each n) by the rules previously offered defining R$^{1-3}$. In the lactams represented by the formula: cyclo-[(CR$^6$R$^7$)$_n$C(O)N(R$^5$)—], all R$^6$ and R$^7$ are preferably hydrogen, or contain a single saturated hydrocarbon radical among the n methylene units, and R$^5$ is a saturated hydrocarbon radical containing 3 to 12 carbon atoms. For example, 1-(saturated hydrocarbon radical)-5-methylpyrrolidin-2-ones.

Representative amide solubilizing agents include but are not limited to: 1-octylpyrrolidin-2-one, 1-decylpyrrolidin-2-one, 1-octyl-5-methylpyrrolidin-2-one, 1-butylcaprolactam, 1-cyclohexylpyrrolidin-2-one, 1-butyl-5-m ethyl piperid-2-one, 1-pentyl-5-methylpiperid-2-one, 1-hexylcaprolactam, 1-hexyl-5-methylpyrrolidin-2-one, 5-methyl-1-pentylpiperid-2-one, 1,3-dimethylpiperid-2-one, 1-methylcaprolactam, 1-butyl-pyrrolidin-2-one, 1,5-dimethylpiperid-2-one, 1-decyl-5-methylpyrrolidin-2-one, 1-dodecylpyrrolid-2-one, N,N-dibutylformamide and N,N-diisopropylacetamide.

Ketone solubilizing agents of the present invention comprise ketones represented by the formula R$^1$C(O)R$^2$, wherein R$^1$ and R$^2$ are independently selected from aliphatic, alicyclic and aryl hydrocarbon radicals having from 1 to 12 carbon atoms, and wherein said ketones have a molecular weight of from about 70 to about 300 atomic mass units. R$^1$ and R$^2$ in said ketones are preferably independently selected from aliphatic and alicyclic hydrocarbon radicals having 1 to 9 carbon atoms. The molecular weight of said ketones is preferably from about 100 to 200 atomic mass units. R$^1$ and R$^2$ may together form a hydrocarbylene radical connected and forming a five, six, or seven-membered ring cyclic ketone, for example, cyclopentanone, cyclohexanone, and cycloheptanone. R$^1$ and R$^2$ may optionally include substituted hydrocarbon radicals, that is, radicals containing non-hydrocarbon substituents selected from halogens (e.g., fluorine, chlorine) and alkoxides (e.g. methoxy). R$^1$ and R$^2$ may optionally include heteroatom-substituted hydrocarbon radicals, that is, radicals, which contain the atoms nitrogen (aza-), oxygen (keto-, oxa-) or sulfur (thia-) in a radical chain otherwise composed of carbon atoms. In general, no more than three non-hydrocarbon substituents and heteroatoms, and preferably no more than one, will be present for each 10 carbon atoms in R$^1$ and R$^2$, and the presence of any such non-hydrocarbon substituents and heteroatoms must be considered in applying the aforementioned molecular weight limitations. Representative R$^1$ and R$^2$ aliphatic, alicyclic and aryl hydrocarbon radicals in the general formula R$^1$C(O)R$^2$ include methyl, ethyl, propyl, isopropyl, butyl, isobutyl, sec-butyl, tert-butyl, pentyl, isopentyl, neopentyl, tert-pentyl, cyclopentyl, cyclohexyl, heptyl, octyl, nonyl, decyl, undecyl, dodecyl and their configurational isomers, as well as phenyl, benzyl, cumenyl, mesityl, tolyl, xylyl and phenethyl.

Representative ketone solubilizing agents include but are not limited to: 2-butanone, 2-pentanone, acetophenone, butyrophenone, hexanophenone, cyclohexanone, cycloheptanone, 2-heptanone, 3-heptanone, 5-methyl-2-hexanone, 2-octanone, 3-octanone, diisobutyl ketone, 4-ethylcyclohexanone, 2-nonanone, 5-nonanone, 2-decanone, 4-decanone, 2-decalone, 2-tridecanone, dihexyl ketone and dicyclohexyl ketone.

Nitrile solubilizing agents of the present invention comprise nitriles represented by the formula R$^1$CN, wherein R$^1$ is selected from aliphatic, alicyclic or aryl hydrocarbon radicals having from 5 to 12 carbon atoms, and wherein said nitriles have a molecular weight of from about 90 to about 200 atomic mass units. R$^1$ in said nitrile solubilizing agents is preferably selected from aliphatic and alicyclic hydrocarbon radicals having 8 to 10 carbon atoms. The molecular weight of said nitrile solubilizing agents is preferably from about 120 to about 140 atomic mass units. R$^1$ may optionally include substituted hydrocarbon radicals, that is, radicals containing non-hydrocarbon substituents selected from halogens (e.g., fluorine, chlorine) and alkoxides (e.g. methoxy). R$^1$ may optionally include heteroatom-substituted hydrocarbon radicals, that is, radicals, which contain the atoms nitrogen (aza-), oxygen (keto-, oxa-) or sulfur (thia-) in a radical chain otherwise composed of carbon atoms. In general, no more than three non-hydrocarbon substituents and heteroatoms, and preferably no more than one, will be present for each 10 carbon atoms in R$^1$, and the presence of any such non-hydrocarbon substituents and heteroatoms must be considered in applying the aforementioned molecular weight limitations. Representative R$^1$ aliphatic, alicyclic and aryl hydrocarbon radicals in the general formula R$^1$CN include pentyl, isopentyl, neopentyl, tert-pentyl, cyclopentyl, cyclohexyl, heptyl, octyl, nonyl, decyl, undecyl, dodecyl and their configurational isomers, as well as phenyl, benzyl, cumenyl, mesityl, tolyl, xylyl and phenethyl. Representative nitrile solubilizing agents include but are not limited to: 1-cyanopentane, 2,2-dimethyl4-cyanopentane, 1-cyanohexane, 1-cyanoheptane, 1-cyanooctane, 2-cyanooctane, 1-cyanononane, 1-cyanodecane, 2-cyanodecane, 1-cyanoundecane and 1-cyanododecane.

Chlorocarbon solubilizing agents of the present invention comprise chlorocarbons represented by the formula $RCl_x$, wherein x is 1 or 2; R is selected from aliphatic and alicyclic hydrocarbon radicals having 1 to 12 carbon atoms; and wherein said chlorocarbons have a molecular weight of from about 100 to about 200 atomic mass units. The molecular weight of said chlorocarbon solubilizing agents is preferably from about 120 to 150 atomic mass units. Representative R aliphatic and alicyclic hydrocarbon radicals in the general formula $RCl_x$ include methyl, ethyl, propyl, isopropyl, butyl, isobutyl, sec-butyl, tert-butyl, pentyl, isopentyl, neopentyl, tert-pentyl, cyclopentyl, cyclohexyl, heptyl, octyl, nonyl, decyl, undecyl, dodecyl and their configurational isomers.

Representative chlorocarbon solubilizing agents include but are not limited to: 3-(chloromethyl)pentane, 3-chloro-3-methylpentane, 1-chlorohexane, 1,6-dichlorohexane, 1-chloroheptane, 1-chlorooctane, 1-chlorononane, 1-chlorodecane, and 1,1,1-trichlorodecane.

Ester solubilizing agents of the present invention comprise esters represented by the general formula $R^1C(O)OR^2$, wherein $R^1$ and $R^2$ are independently selected from linear and cyclic, saturated and unsaturated, alkyl and aryl radicals. Preferred esters consist essentially of the elements C, H and O, have a molecular weight of from about 80 to about 550 atomic mass units.

Representative esters include but are not limited to: $(CH_3)_2CHCH_2O(O)C(CH_2)_{2-4}(O)COCH_2CH(CH_3)_2$ (diisobutyl dibasic ester), ethyl hexanoate, ethyl heptanoate, n-butyl propionate, n-propyl propionate, ethyl benzoate, di-n-propyl phthalate, benzoic acid ethoxyethyl ester, dipropyl carbonate, "Exxate 700" (a commercial $C_7$ alkyl acetate), "Exxate 800" (a commercial $C_8$ alkyl acetate), dibutyl phthalate, and tert-butyl acetate.

Lactone solubilizing agents of the present invention comprise lactones represented by structures [A], [B], and [C]:

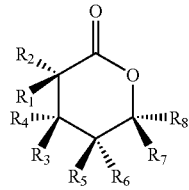

[A]

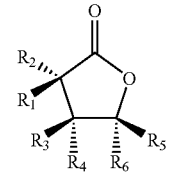

[B]

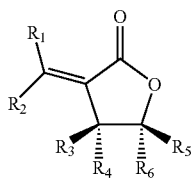

[C]

These lactones contain the functional group —C(O)O— in a ring of six (A), or preferably five atoms (B), wherein for structures [A] and [B], $R_1$ through $R_8$ are independently selected from hydrogen or linear, branched, cyclic, bicyclic, saturated and unsaturated hydrocarbyl radicals. Each $R_1$ though $R_8$ may be connected forming a ring with another $R_1$ through $R_8$. The lactone may have an exocyclic alkylidene group as in structure [C], wherein $R_1$ through $R_6$ are independently selected from hydrogen or linear, branched, cyclic, bicyclic, saturated and unsaturated hydrocarbyl radicals. Each $R_1$ though $R_6$ may be connected forming a ring with another $R_1$ through $R_6$. The lactone solubilizing agents have a molecular weight range of from about 80 to about 300 atomic mass units, preferred from about 80 to about 200 atomic mass units.

Representative lactone solubilizing agents include but are not limited to the compounds listed in Table 7.

TABLE 7

| Additive | Molecular Structure | Molecular Formula | Molecular Weight (amu) |
| --- | --- | --- | --- |
| (E,Z)-3-ethylidene-5-methyl-dihydro-furan-2-one | 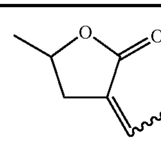 | $C_7H_{10}O_2$ | 126 |
| (E,Z)-3-propylidene-5-methyl-dihydro-furan-2-one | 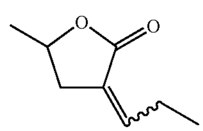 | $C_8H_{12}O_2$ | 140 |
| (E,Z)-3-butylidene-5-methyl-dihydro-furan-2-one | 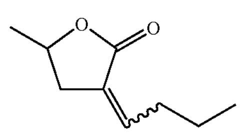 | $C_9H_{14}O_2$ | 154 |

TABLE 7-continued

| Additive | Molecular Structure | Molecular Formula | Molecular Weight (amu) |
|---|---|---|---|
| (E,Z)-3-pentylidene-5-methyl-dihydro-furan-2-one | 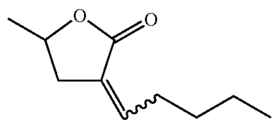 | $C_{10}H_{16}O_2$ | 168 |
| (E,Z)-3-Hexylidene-5-methyl-dihydro-furan-2-one | 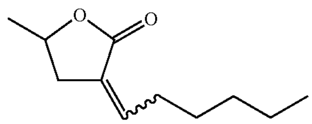 | $C_{11}H_{18}O_2$ | 182 |
| (E,Z)-3-Heptylidene-5-methyl-dihydro-furan-2-one | 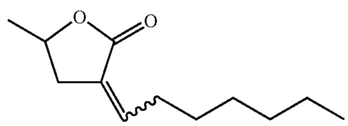 | $C_{12}H_{20}O_2$ | 196 |
| (E,Z)-3-octylidene-5-methyl-dihydro-furan-2-one | 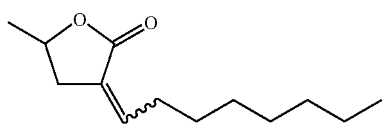 | $C_{13}H_{22}O_2$ | 210 |
| (E,Z)-3-nonylidene-5-methyl-dihydro-furan-2-one | 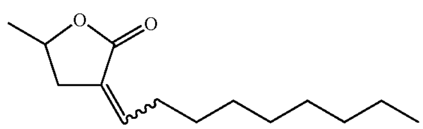 | $C_{14}H_{24}O_2$ | 224 |
| (E,Z)-3-decylidene-5-methyl-dihydro-furan-2-one | 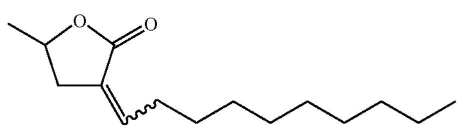 | $C_{15}H_{26}O_2$ | 238 |
| (E,Z)-3-(3,5,5-(trimethylhexylidene)-5-methyl-dihydrofuran-2-one | 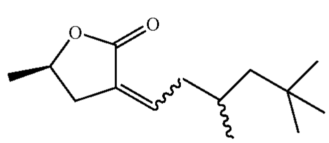 | $C_{14}H_{24}O_2$ | 224 |
| (E,Z)-3-cyclohexylmethylidene-5-methyl-dihydrofuran-2-one | 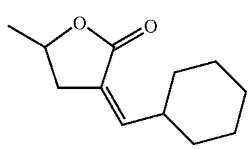 | $C_{12}H_{18}O_2$ | 194 |
| gamma-octalactone | 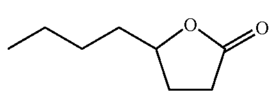 | $C_8H_{14}O_2$ | 142 |
| gamma-nonalactone | 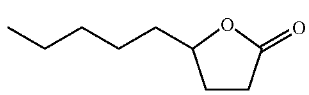 | $C_9H_{16}O_2$ | 156 |
| gamma-decalactone | 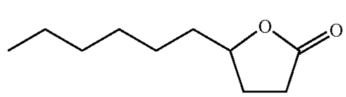 | $C_{10}H_{18}O_2$ | 170 |
| gamma-undecalactone | 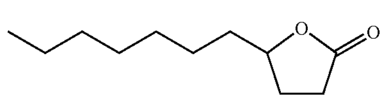 | $C_{11}H_{20}O_2$ | 184 |

TABLE 7-continued

| Additive | Molecular Structure | Molecular Formula | Molecular Weight (amu) |
|---|---|---|---|
| gamma-dodecalactone | 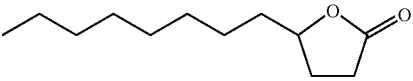 | $C_{12}H_{22}O_2$ | 198 |
| 3-hexyldihydro-furan-2-one | 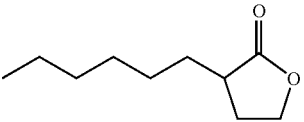 | $C_{10}H_{18}O_2$ | 170 |
| 3-heptyldihydro-furan-2-one | 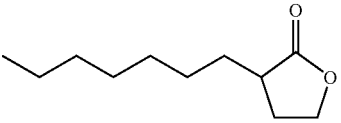 | $C_{11}H_{20}O_2$ | 184 |
| cis-3-ethyl-5-methyl-dihydro-furan-2-one | 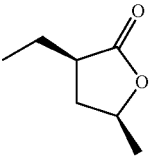 | $C_7H_{12}O_2$ | 128 |
| cis-(3-propyl-5-methyl)-dihydro-furan-2-one | 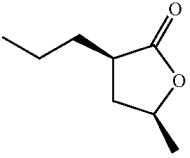 | $C_8H_{14}O_2$ | 142 |
| cis-(3-butyl-5-methyl)-dihydro-furan-2-one | 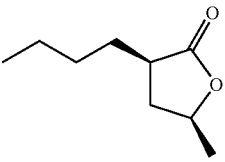 | $C_9H_{16}O_2$ | 156 |
| cis-(3-pentyl-5-methyl)-dihydro-furan-2-one | 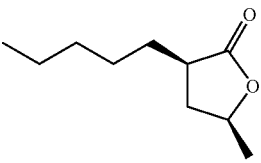 | $C_{10}H_{18}O_2$ | 170 |
| cis-3-hexyl-5-methyl-dihydro-furan-2-one | 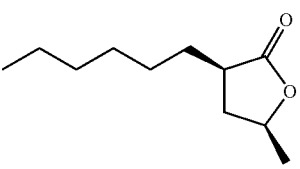 | $C_{11}H_{20}O_2$ | 184 |
| cis-3-heptyl-5-methyl-dihydro-furan-2-one | 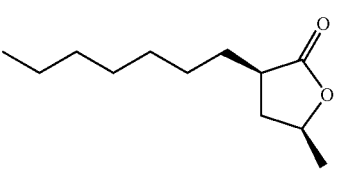 | $C_{12}H_{22}O_2$ | 198 |

TABLE 7-continued

| Additive | Molecular Structure | Molecular Formula | Molecular Weight (amu) |
|---|---|---|---|
| cis-3-octyl-5-methyl-dihydro-furan-2-one | 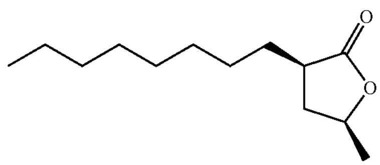 | $C_{13}H_{24}O_2$ | 212 |
| cis-3-(3,5,5-trimethylhexyl)-5-methyl-dihydro-furan-2-one | 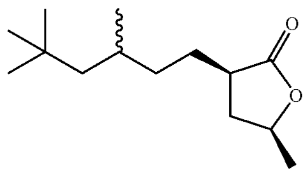 | $C_{14}H_{26}O_2$ | 226 |
| cis-3-cyclohexylmethyl-5-methyl-dihydro-furan-2-one | 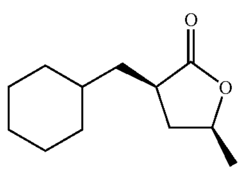 | $C_{12}H_{20}O_2$ | 196 |
| 5-methyl-5-hexyl-dihydro-furan-2-one | 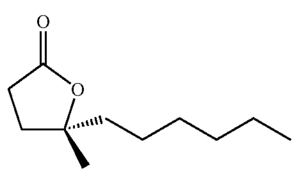 | $C_{11}H_{20}O_2$ | 184 |
| 5-methyl-5-octyl-dihydro-furan-2-one | 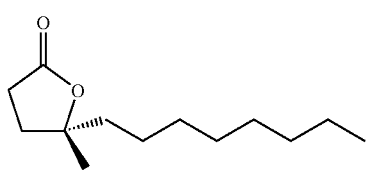 | $C_{13}H_{24}O_2$ | 212 |
| Hexahydro-isobenzofuran-1-one | 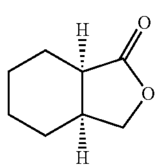 | $C_8H_{12}O_2$ | 140 |
| delta-decalactone | 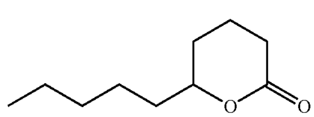 | $C_{10}H_{18}O_2$ | 170 |
| delta-undecalactone | 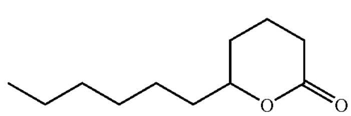 | $C_{11}H_{20}O_2$ | 184 |
| delta-dodecalactone | 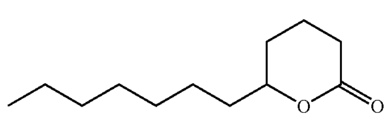 | $C_{12}H_{22}O_2$ | 198 |

TABLE 7-continued

| Additive | Molecular Structure | Molecular Formula | Molecular Weight (amu) |
|---|---|---|---|
| mixture of 4-hexyl-dihydrofuran-2-one and 3-hexyl-dihydro-furan-2-one | 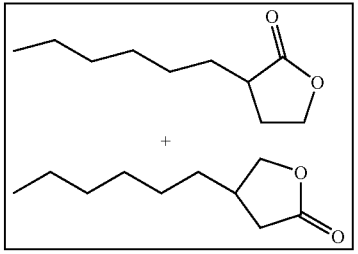 | $C_{10}H_{18}O_2$ | 170 |

Lactone solubilizing agents generally have a kinematic viscosity of less than about 7 centistokes at 40° C. For instance, gamma-undecalactone has kinematic viscosity of 5.4 centistokes and cis-(3-hexyl-5-methyl)dihydrofuran-2-one has viscosity of 4.5 centistokes, both at 40° C. Lactone solubilizing agents may be available commercially or prepared by methods as described in U. S. patent application Ser. No. 10/910,495 (inventors being P. J. Fagan and C. J. Brandenburg), filed Aug.3, 2004, incorporated herein by reference.

Aryl ether solubilizing agents of the present invention comprise aryl ethers represented by the formula $R^1OR^2$, wherein: $R^1$ is selected from aryl hydrocarbon radicals having from 6 to 12 carbon atoms; $R^2$ is selected from aliphatic hydrocarbon radicals having from 1 to 4 carbon atoms; and wherein said aryl ethers have a molecular weight of from about 100 to about 150 atomic mass units. Representative $R^1$ aryl radicals in the general formula $R^1OR^2$ include phenyl, biphenyl, cumenyl, mesityl, tolyl, xylyl, naphthyl and pyridyl. Representative $R^2$ aliphatic hydrocarbon radicals in the general formula $R^1OR^2$ include methyl, ethyl, propyl, isopropyl, butyl, isobutyl, sec-butyl and tert-butyl. Representative aromatic ether solubilizing agents include but are not limited to: methyl phenyl ether (anisole), 1,3-dimethyoxybenzene, ethyl phenyl ether and butyl phenyl ether.

Fluoroether solubilizing agents of the present invention comprise those represented by the general formula $R^1OCF_2CF_2H$, wherein $R^1$ is selected from aliphatic and alicyclic hydrocarbon radicals having from about 5 to about 15 carbon atoms, preferably primary, linear, saturated, alkyl radicals. Representative fluoroether solubilizing agents include but are not limited to: $C_8H_{17}OCF_2CF_2H$ and $C_6H_{13}OCF_2CF_2H$. It should be noted that if the refrigerant is a fluoroether, then the solubilizing agent may not be the same fluoroether.

Fluoroether solubilizing agents may further comprise ethers derived from fluoro-olefins and polyols. The fluoro-olefins may be of the type $CF_2=CXY$, wherein X is hydrogen, chlorine or fluorine, and Y is chlorine, fluorine, $CF_3$ or $OR_f$, wherein $R_f$ is $CF_3$, $C_2F_5$, or $C_3F_7$. Representative fluoro-olefins are tetrafluoroethylene, chlorotrifluoroethylene, hexafluoropropylene, and perfluoromethylvinyl ether. The polyols may be of the type $HOCH_2CRR'(C)_z(CHOH)_xCH_2(CH_2OH)_y$, wherein R and R' are hydrogen, or $CH_3$, or $C_2H_5$ and wherein x is an integer from 0-4, y is an integer from 0-3 and z is either zero or 1. Representative polyols are trimethylol propane, pentaerythritol, butanediol, and ethylene glycol.

1,1,1-Trifluoroalkane solubilizing agents of the present invention comprise 1,1,1-trifluoroalkanes represented by the general formula $CF_3R^1$, wherein $R^1$ is selected from aliphatic and alicyclic hydrocarbon radicals having from about 5 to about 15 carbon atoms, preferably primary, linear, saturated alkyl radicals. Representative 1,1,1-trifluoroalkane solubilizing agents include but are not limited to: 1,1,1-trifluorohexane and 1,1,1-trifluorododecane.

Solubilizing agents of the present invention may be present as a single compound, or may be present as a mixture of more than one solubilizing agent. Mixtures of solubilizing agents may contain two solubilizing agents from the same class of compounds, say two lactones, or two solubilizing agents from two different classes, such as a lactone and a polyoxyalkylene glycol ether.

In the present compositions comprising refrigerant and UV fluorescent dye, or comprising heat transfer fluid and UV fluorescent dye, from about 0.001 weight percent to about 1.0 weight percent of the compositions is UV dye, preferably from about 0.005 weight percent to about 0.5 weight percent, and most preferably from 0.01 weight percent to about 0.25 weight percent.

Solubility of these UV fluorescent dyes in refrigerants and heat transfer fluids may be poor. Therefore, methods for introducing these dyes into the refrigeration or air-conditioning apparatus have been awkward, costly and time consuming. U.S. Pat. No. RE 36,951 describes a method, which utilizes a dye powder, solid pellet or slurry of dye that may be inserted into a component of the refrigeration or air-conditioning apparatus. As refrigerant and lubricant are circulated through the apparatus, the dye is dissolved or dispersed and carried throughout the apparatus. Numerous other methods for introducing dye into a refrigeration or air-conditioning apparatus are described in the literature.

Ideally, the UV fluorescent dye could be dissolved in the refrigerant itself thereby not requiring any specialized method for introduction to the refrigeration or air-conditioning apparatus. The present invention relates to compositions including UV fluorescent dye, which may be introduced into the system in the refrigerant. The inventive compositions will allow the storage and transport of dye containing refrigerant and heat transfer fluid even at low temperatures while maintaining the dye in solution.

In the present compositions comprising refrigerant, UV fluorescent dye and solubilizing agent, or comprising heat transfer fluid, UV fluorescent dye and solubilizing agent, from about 1 to about 50 weight percent, preferably from about 2 to about 25 weight percent, and most preferably from about 5 to about 15 weight percent of the combined composition is solubilizing agent in the refrigerant or heat transfer fluid. In the compositions of the present invention the UV fluorescent dye is present in a concentration from about 0.001 weight percent to about 1.0 weight percent in the refrigerant or heat transfer fluid, preferably from 0.005 weight percent to about 0.5 weight percent, and most preferably from 0.01 weight percent to about 0.25 weight percent.

Optionally, commonly used refrigeration or air-conditioning system additives may be added, as desired, to compositions of the present invention in order to enhance performance and system stability. These additives are known in the field of refrigeration and air-conditioning, and include, but are not limited to, anti wear agents, extreme pressure lubricants, corrosion and oxidation inhibitors, metal surface deactivators, free radical scavengers, and foam control agents. In general, these additives are present in the inventive compositions in small amounts relative to the overall composition. Typically concentrations of from less than about 0.1 weight percent to as much as about 3 weight percent of each additive are used. These additives are selected on the basis of the individual system requirements. These additives include members of the triaryl phosphate family of EP (extreme pressure) lubricity additives, such as butylated triphenyl phosphates (BTPP), or other alkylated triaryl phosphate esters, e.g. Syn-0-Ad 8478 from Akzo Chemicals, tricresyl phosphates and related compounds. Additionally, the metal dialkyl dithiophosphates (e.g. zinc dialkyl dithiophosphate (or ZDDP), Lubrizol 1375 and other members of this family of chemicals may be used in compositions of the present invention. Other antiwear additives include natural product oils and asymmetrical polyhydroxyl lubrication additives, such as Synergol TMS (International Lubricants). Similarly, stabilizers such as anti oxidants, free radical scavengers, and water scavengers may be employed. Compounds in this category can include, but are not limited to, butylated hydroxy toluene (BHT) and epoxides.

Solubilizing agents such as ketones may have an objectionable odor, which can be masked by addition of an odor masking agent or fragrance. Typical examples of odor masking agents or fragrances may include Evergreen, Fresh Lemon, Cherry, Cinnamon, Peppermint, Floral or Orange Peel, all commercially available, as well as d-limonene and pinene. Such odor masking agents may be used at concentrations of from about 0.001 % to as much as about 15% by weight based on the combined weight of odor masking agent and solubilizing agent.

The present invention further relates to a method of using the refrigerant or heat transfer fluid compositions further comprising ultraviolet fluorescent dye, and optionally, solubilizing agent, in refrigeration or air-conditioning apparatus. The method comprises introducing the refrigerant or heat transfer fluid composition into the refrigeration or air-conditioning apparatus. This may be done by dissolving the UV fluorescent dye in the refrigerant or heat transfer fluid composition in the presence of a solubilizing agent and introducing the combination into the apparatus. Alternatively, this may be done by combining solubilizing agent and UV fluorescent dye and introducing said combination into refrigeration or air-conditioning apparatus containing refrigerant and/or heat transfer fluid. The resulting composition may be used in the refrigeration or air-conditioning apparatus.

The present invention further relates to a method of using the refrigerant or heat transfer fluid compositions comprising ultraviolet fluorescent dye to detect leaks. The presence of the dye in the compositions allows for detection of leaking refrigerant in the refrigeration or air-conditioning apparatus. Leak detection helps to address, resolve or prevent inefficient operation of the apparatus or system or equipment failure. Leak detection also helps one contain chemicals used in the operation of the apparatus.

The method comprises providing the composition comprising refrigerant and ultra-violet fluorescent dye, or comprising heat transfer fluid and ultra-violet fluorescent dye as described herein, and optionally, a solubilizing agent as described herein, to refrigeration and air-conditioning apparatus and employing a suitable means for detecting the UV fluorescence at a leak point. Suitable means for detecting the dye include, but are not limited to, ultra-violet lamp, often referred to as a "black light" or "blue light". Such ultra-violet lamps are commercially available from numerous sources specifically designed for this purpose. Once the ultra-violet fluorescent dye containing composition has been introduced to the refrigeration or air-conditioning apparatus and has been allowed to circulate throughout the system, a leak can be found by shining said ultra-violet lamp on the apparatus and observing the fluorescence of the dye in the vicinity of any leak point.

The present invention further relates to a method of using the compositions of the present invention for producing refrigeration or heat, wherein the method comprises producing refrigeration by evaporating said composition in the vicinity of a body to be cooled and thereafter condensing said composition; or producing heat by condensing said composition in the vicinity of the body to be heated and thereafter evaporating said composition.

Mechanical refrigeration is primarily an application of thermodynamics wherein a cooling medium, such as a refrigerant, goes through a cycle so that it can be recovered for reuse. Commonly used cycles include vapor-compression, absorption, steam-jet or steam-ejector, and air.

Vapor-compression refrigeration systems include an evaporator, a compressor, a condenser, and an expansion device. A vapor-compression cycle re-uses refrigerant in multiple steps producing a cooling effect in one step and a heating effect in a different step. The cycle can be described simply as follows. Liquid refrigerant enters an evaporator through an expansion device, and the liquid refrigerant boils in the evaporator at a low temperature to form a gas and produce cooling. The low-pressure gas enters a compressor where the gas is compressed to raise its pressure and temperature. The higher-pressure (compressed) gaseous refrigerant then enters the condenser in which the refrigerant condenses and discharges its heat to the environment. The refrigerant returns to the expansion device through which the liquid expands from the higher-pressure level in the condenser to the low-pressure level in the evaporator, thus repeating the cycle.

There are various types of compressors that may be used in refrigeration applications. Compressors can be generally classified as reciprocating, rotary, jet, centrifugal, scroll, screw or axial-flow, depending on the mechanical means to compress the fluid, or as positive-displacement (e.g., reciprocating, scroll or screw) or dynamic (e.g., centrifugal or jet), depending on how the mechanical elements act on the fluid to be compressed.

Either positive displacement or dynamic compressors may be used in the present inventive process. A centrifugal type compressor is the preferred equipment for the present refrigerant compositions.

A centrifugal compressor uses rotating elements to accelerate the refrigerant radially, and typically includes an impeller and diffuser housed in a casing. Centrifugal compressors usually take fluid in at an impeller eye, or central inlet of a circulating impeller, and accelerate it radially outward. Some static pressure rise occurs in the impeller, but most of the pressure rise occurs in the diffuser section of the casing, where velocity is converted to static pressure. Each impeller-diffuser set is a stage of the compressor. Centrifugal compressors are built with from 1 to 12 or more stages, depending on the final pressure desired and the volume of refrigerant to be handled.

The pressure ratio, or compression ratio, of a compressor is the ratio of absolute discharge pressure to the absolute inlet pressure. Pressure delivered by a centrifugal compressor is practically constant over a relatively wide range of capacities.

Positive displacement compressors draw vapor into a chamber, and the chamber decreases in volume to compress the vapor. After being compressed, the vapor is forced from the chamber by further decreasing the volume of the chamber to zero or nearly zero. A positive displacement compressor can build up a pressure, which is limited only by the volumetric efficiency and the strength of the parts to withstand the pressure.

Unlike a positive displacement compressor, a centrifugal compressor depends entirely on the centrifugal force of the high-speed impeller to compress the vapor passing through the impeller. There is no positive displacement, but rather what is called dynamic-compression.

The pressure a centrifugal compressor can develop depends on the tip speed of the impeller. Tip speed is the speed of the impeller measured at its tip and is related to the diameter of the impeller and its revolutions per minute. The capacity of the centrifugal compressor is determined by the size of the passages through the impeller. This makes the size of the compressor more dependent on the pressure required than the capacity.

Because of its high-speed operation, a centrifugal compressor is fundamentally a high volume, low-pressure machine. A centrifugal compressor works best with a low-pressure refrigerant, such as trichlorofluoromethane (CFC-11) or 1,2,2-trichlorotrifluoroethane (CFC-113).

Large centrifugal compressors typically operate at 3000 to 7000 revolutions per minute (rpm). Small turbine centrifugal compressors are designed for high speeds, from about 40,000 to about 70,000 (rpm), and have small impeller sizes, typically less than 0.15 meters.

A multi-stage impeller may be used in a centrifugal compressor to improve compressor efficiency thus requiring less power in use. For a two-stage system, in operation, the discharge of the first stage impeller goes to the suction intake of a second impeller. Both impellers may operate by use of a single shaft (or axle). Each stage can build up a compression ratio of about 4 to 1; that is, the absolute discharge pressure can be four times the absolute suction pressure. An example of a two-stage centrifugal compressor system, in this case for automotive applications, is described in U.S. Pat. No. 5,065,990, incorporated herein by reference.

The compositions of the present invention suitable for use in a refrigeration or air-conditioning systems employing a centrifugal compressor comprise at least one of:

HFC-63-14mcee and cyclohexane;
HFC-63-14mcee and 2,2,3-trimethylbutane;
HFC-63-14mcee and 2,4-dimethylpentane;
HFC-63-14mcee and 3,3-dimethylpentane;
HFC-63-14mcee and 2,3-dimethylpentane
HFC-63-14mcee and 2-methylhexane;
HFC-63-14mcee and 3-methylhexane,
HFC-63-14mcee and isooctane;
HFC-63-14mcee and 2-bromopropane;
HFC-63-14mcee and 1-bromopropane;
HFC-63-14mcee and 1,2-dichloroethane;
HFC-63-14mcee and 1,1-dichloroethane;
HFC-63-14mcee and fluorobenzene;
HFC-63-14mcee and o-difluorobenzene;
HFC-63-14mcee and m-difluorobenzene;
HFC-63-14mcee and p-difluorobenzene;
HFC-63-14mcee and trichloroethylene;
HFC-63-14mcee and methanol;
HFC-63-14mcee and ethanol;
HFC-63-14mcee and 2-methyl-2-propanol;
HFC-63-14mcee and 2,2-dimethyl-1,3-dioxolane;
HFC-63-14mcee and acetonitrile;
HFC-63-14mcee and ethyl acetate;
HFC-63-14mcee and methyl propionate;
HFC-63-14mcee and n-propyl formate;
HFC-63-14mcee and dimethylcarbonate;
HFC-63-14mcee and isopropyl acetate;
HFC-63-14mcee and 2,2,2-trifluoroethanol;
HFC-63-14mcee and isopropanol;
HFC-63-14mcee and 2,2,3,3,3-pentafluoro-1-propanol;
HFC-63-14mcee and 2,2,3,3-tetrafluoro-1-propanol; and
HFC-63-14mcee and 1,1,1,3,3,3-hexafluoro-2-propanol.

These above-listed compositions are also suitable for use in a multi-stage centrifugal compressor, preferably a two-stage centrifugal compressor apparatus.

The compositions of the present invention may be used in stationary air-conditioning, heat pumps or mobile air-conditioning and refrigeration systems. Stationary air-conditioning and heat pump applications include window, ductless, ducted, packaged terminal, chillers and commercial, including packaged rooftop. Refrigeration applications include domestic or home refrigerators and freezers, ice machines, self-contained coolers and freezers, walk-in coolers and freezers and transport refrigeration systems.

The compositions of the present invention may additionally be used in air-conditioning, heating and refrigeration systems that employ fin and tube heat exchangers, microchannel heat exchangers and vertical or horizontal single pass tube or plate type heat exchangers.

Conventional microchannel heat exchangers may not be ideal for the low pressure refrigerant compositions of the present invention. The low operating pressure and density result in high flow velocities and high frictional losses in all components. In these cases, the evaporator design may be modified. Rather than several microchannel slabs connected in series (with respect to the refrigerant path) a single slab/single pass heat exchanger arrangement may be used. Therefore, a preferred heat exchanger for the low pressure refrigerants of the present invention is a single slab/single pass heat exchanger.

In addition to two-stage or other multi-stage centrifugal compressor apparatus, the following compositions of the present invention are suitable for use in refrigeration or air-conditioning apparatus employing a single slab/single pass heat exchanger:

HFC-63-14mcee and cyclohexane;
HFC-63-14mcee and 2,2,3-trimethylbutane;
HFC-63-14mcee and 2,4-dimethylpentane;
HFC-63-14mcee and 3,3-dimethylpentane;
HFC-63-14mcee and 2,3-dimethylpentane
HFC-63-14mcee and 2-methylhexane;
HFC-63-14mcee and 3-methylhexane,
HFC-63-14mcee and isooctane;
HFC-63-14mcee and 2-bromopropane;
HFC-63-14mcee and 1-bromopropane;
HFC-63-14mcee and 1,2-dichloroethane;
HFC-63-14mcee and 1,1-dichloroethane;
HFC-63-14mcee and fluorobenzene;
HFC-63-14mcee and o-difluorobenzene;

HFC-63-14mcee and m-difluorobenzene;
HFC-63-14mcee and p-difluorobenzene;
HFC-63-14mcee and trichloroethylene;
HFC-63-14mcee and methanol;
HFC-63-14mcee and ethanol;
HFC-63-14mcee and 2-methyl-2-propanol;
HFC-63-14mcee and 2,2-dimethyl-1,3-dioxolane;
HFC-63-14mcee and acetonitrile;
HFC-63-14mcee and ethyl acetate;
HFC-63-14mcee and methyl propionate;
HFC-63-14mcee and n-propyl formate;
HFC-63-14mcee and dimethylcarbonate;
HFC-63-14mcee and isopropyl acetate;
HFC-63-14mcee and 2,2,2-trifluoroethanol;
HFC-63-14mcee and isopropanol;
HFC-63-14mcee and 2,2,3,3,3-pentafluoro-1-propanol;
HFC-63-14mcee and 2,2,3,3-tetrafluoro-1-propanol; and
HFC-63-14mcee and 1,1,1,3,3,3-hexafluoro-2-propanol.

The compositions of the present invention are particularly useful in small turbine centrifugal compressors, which can be used in auto and window air-conditioning or heat pumps as well as other applications. These high efficiency miniature centrifugal compressors may be driven by an electric motor and can therefore be operated independently of the engine speed. A constant compressor speed allows the system to provide a relatively constant cooling capacity at all engine speeds. This provides an opportunity for efficiency improvements especially at higher engine speeds as compared to a conventional R-134a automobile air-conditioning system. When the cycling operation of conventional systems at high driving speeds is taken into account, the advantage of these low pressure systems becomes even greater.

Some of the low pressure refrigerant fluids of the present invention may be suitable as drop-in replacements for CFC-113 in existing centrifugal equipment.

The present invention further relates to a process for producing refrigeration comprising evaporating the compositions of the present invention in the vicinity of a body to be cooled, and thereafter condensing said compositions.

The present invention further relates to a process for producing heat comprising condensing the compositions of the present invention in the vicinity of a body to be heated, and thereafter evaporating said compositions.

The present invention further relates to a process for transfer of heat from a heat source to a heat sink wherein the compositions of the present invention serve as heat transfer fluids. Said process for heat transfer comprises transferring the compositions of the present invention from a heat source to a heat sink.

Heat transfer fluids are utilized to transfer, move or remove heat from one space, location, object or body to a different space, location, object or body by radiation, conduction, or convection. A heat transfer fluid may function as a secondary coolant by providing means of transfer for cooling (or heating) from a remote refrigeration (or heating) system. In some systems, the heat transfer fluid may remain in a constant state throughout the transfer process (i.e., not evaporate or condense). Alternatively, evaporative cooling processes may utilize heat transfer fluids as well.

A heat source may be defined as any space, location, object or body from which it is desirable to transfer, move or remove heat. Examples of heat sources may be spaces (open or enclosed) requiring refrigeration or cooling, such as refrigerator or freezer cases in a supermarket, building spaces requiring air-conditioning, or the passenger compartment of an automobile requiring air-conditioning. A heat sink may be defined as any space, location, object or body capable of absorbing heat. A vapor compression refrigeration system is one example of such a heat sink.

EXAMPLES

In the following examples, HFC-63-14mcee is 1,1,1,2,2,3,4,5,5,6,6,7,7,7-tetradecafluoroheptane, trans-DCE is trans-1,2-dichloroethylene, MeOH is methanol, EtOH is ethanol, and IPA is isopropanol.

Example 1

Fluorolubricant Solubility

The ability of HFC-63-14mcee to solubilize a fluorolubricant was determined in the following experiment. A known amount of HFC-63-14mcee solvent was added to a beaker. A known amount of lubricant (Krytox® GPL 100) was then added to the beaker. More lubricant was added in incremental steps until the mixture was approximately 50 weight percent solvent and 50 weight percent lubricant. The solution remained clear with no haziness, cloudiness, or phase separation. This experiment indicates that the Krytox® GPL 100 fluorolubricant is completely soluble in the HFC-63-14mcee solvent at 50 weight percent and below.

Example 2

Comparative Example

Disks are coated with fluorolubricant using two different solvent systems. The solutions being used are 0.05 percent (weight/weight) Fomblin Z-Dol® in Vertrel® XF and 0.05 percent (weight/weight) Fomblin Z-Dol® in HFC-63-14mcee. In both cases, the fluorolubricant is completely miscible with the solvent. The disks are standard magnetic media, which are 95-mm nickel-phosphorus (NiP, about 10 μm thick) plated aluminum substrates with magnetic coatings. On top of the magnetic coatings are deposited a diamond-like-carbon (DLC) film. The disks are mounted vertically on a V-shaped mandrel and dip coated in a bath of each of the solutions. The disks are pulled vertically out of the bath at a steady speed of 1 mm/s. Evaporation of the solvent is accomplished using standard techniques at about 40° C.

The resulting disks are examined visually and the presence of any irregularities is noted. The disk coated using the HFC-63-14mcee/Fomblin Z-Dol® solution shows no evidence of "rabbit ears", while the disk coated with from the Vertrel® XF/Fomblin Z-Dol® solution exhibits the "rabbit ears" phenomenon.

Example 3

Distillation of HFC-63-14mcee/trans-DCE/methanol composition

A solution containing about 24 weight percent HFC-63-14mcee, about 70 weight percent trans-1,2-dichloroethylene (trans-DCE), and about 6 weight percent methanol (MeOH) was prepared in a suitable container and mixed thoroughly. The solution was distilled in a five plate Oldershaw distillation column (7 cm diameter, 40 cm height) using reflux ratio as noted below. Head and pot temperatures were read directly to 1° C. The distillation was performed at a pressure of 760 mm Hg with 30 minutes between cuts. Distillate compositions were determined by gas chromatography. Results are summarized in Table 8.

TABLE 8

| Sample | Composition (weight percent) | | | Reflux ratio | Flask temp (° C.) | Head temp (° C.) |
|---|---|---|---|---|---|---|
| | HFC-63-14mcee | Trans-DCE | MeOH | | | |
| Cut 1 | 18.34 | 73.53 | 8.13 | 20:1 | 40 | 40 |
| Cut 2 | 18.30 | 73.55 | 8.15 | 20:1 | 40 | 40 |
| Cut 3 | 18.94 | 73.04 | 8.02 | 15:1 | 40 | 40 |
| Cut 4 | 19.09 | 72.92 | 7.99 | 10:1 | 40 | 40 |
| Cut 5 | 18.64 | 73.13 | 8.23 | 10:1 | 42 | 40 |
| Heel | 27.66 | 67.73 | 4.61 | Na | na | na |

Analysis of the above data indicates small differences in head temperatures and distillate compositions as the distillation progressed. A statistical analysis of the data demonstrates that the true ternary azeotrope of HFC-63-14mcee, trans-DCE, and methanol has the following characteristics at atmospheric pressure:

| HFC-63-14mcee | 18.7 ± 0.4 weight percent |
|---|---|
| Trans-DCE | 73.2 ± 0.3 weight percent |
| Methanol | 8.1 ± 0.1 weight percent |

Example 4

Distillation of HFC-63-14mcee/trans-DCE/ethanol composition

A solution containing about 24 weight percent HFC-63-14mcee, about 70 weight percent trans-1,2-dichloroethylene (trans-DCE), and about 6 percent ethanol (EtOH) was prepared in a suitable container and mixed thoroughly. The solution was distilled in a five plate Oldershaw distillation column (7 cm diameter, 40 cm height) using a reflux ratio of 10:1. Head and pot temperatures were read directly to 1° C. The distillation was performed at a pressure of 760 mm Hg with 30 minutes between cuts. Distillate compositions were determined by gas chromatography. Results are summarized in Table 9.

TABLE 9

| Sample | Composition (weight percent) | | | Flask temp (° C.) | Head temp (° C.) |
|---|---|---|---|---|---|
| | HFC-63-14mcee | Trans-DCE | EtOH | | |
| Cut 1 | 21.78 | 73.86 | 4.36 | 44 | 45 |
| Cut 2 | 21.78 | 73.82 | 4.40 | 44 | 45 |
| Cut 3 | 21.71 | 73.88 | 4.41 | 44 | 45 |
| Cut 4 | 21.88 | 73.64 | 4.48 | 44 | 45 |
| Cut 5 | 22.02 | 73.48 | 4.50 | 44 | 45 |
| Heel | 26.68 | 65.56 | 7.76 | na | na |

Analysis of the above data indicates small differences in head temperatures and distillate compositions as the distillation progressed. A statistical analysis of the data demonstrates that the true ternary azeotrope of HFC-63-14mcee, trans-DCE, and ethanol has the following characteristics at atmospheric pressure:

| HFC-63-14mcee | 21.8 ± 0.1 weight percent |
|---|---|
| Trans-DCE | 73.8 ± 0.2 weight percent |
| Ethanol | 4.4 ± 0.06 weight percent |

Example 5

Distillation of HFC-63-14mcee/trans-DCE/isopropanol composition

A solution containing about 24 weight percent HFC-63-14mcee, about 70.0 weight percent trans-1,2-dichloroethylene (trans-DCE), and about 6 weight percent isopropanol (IPA) was prepared in a suitable container and mixed thoroughly. The solution was distilled in a five plate Oldershaw distillation column (7 cm diameter, 40 cm height) using a reflux ratio of 10:1. Head and pot temperatures were read directly to 1° C. The distillation was performed at a pressure of 760 mm Hg with 30 minutes between cuts. Distillate compositions were determined by gas chromatography. Results are summarized in Table 10.

TABLE 10

| Sample | Composition (weight percent) | | | Flask temp (° C.) | Head temp (° C.) |
|---|---|---|---|---|---|
| | HFC-63-14mcee | Trans-DCE | IPA | | |
| Cut 1 | 22.46 | 75.11 | 2.43 | 46 | 45 |
| Cut 2 | 22.55 | 74.97 | 2.48 | 46 | 45 |
| Cut 3 | 22.60 | 74.91 | 2.49 | 46 | 45 |
| Cut 4 | 22.56 | 74.92 | 2.52 | 46 | 45 |
| Cut 5 | 22.61 | 74.84 | 2.55 | 46 | 45 |
| Heel | 26.05 | 63.83 | 10.12 | na | na |

Analysis of the above data indicates small differences in head temperatures and distillate compositions as the distillation progressed. A statistical analysis of the data demonstrates that the true ternary azeotrope of HFC-63-14mcee, trans-DCE, and isopropanol has the following characteristics at atmospheric pressure:

| HFC-63-14mcee | 22.5 ± 0.6 weight percent |
|---|---|
| Trans-DCE | 75.0 ± 0.1 weight percent |
| Isopropanol | 2.5 ± 0.05 weight percent |

Example 6

Solubility

Compositions of the present invention were tested for room temperature solubility with mineral oil, motor oil (600W, non-detergent) and rosin (water white). Solubility, in weight percent, was measured by weighing and placing an amount of fluid in a suitable container, then slowly adding a composition of the present invention until the fluid is completely dissolved. Results are shown in Table 11 below.

TABLE 11

| Composition (wt %) | Solubility (weight percent) | | |
|---|---|---|---|
| | Mineral oil | Motor oil | Rosin |
| HFC-63-14mcee/trans-DCE/MeOH (20/74/6) | 17 | 13 | 18 |
| HFC-63-14mcee/trans-DCE/MeOH (24/70/6) | 11 | — | 14 |
| HFC-63-14mcee/trans-DCE/MeOH (18.7/73.2/8.1) | 20 | — | 21 |
| HFC-63-14mcee/trans-DCE/EtOH (21.8/73.8/4.4) | 12 | 9 | 14 |
| HFC-63-14mcee/trans-DCE/IPA (22.5/75.0/2.5) | 9 | 7 | 13 |

Example 7

Defluxing Performance

The compositions of the present invention are effective for cleaning ionic contamination (flux residue) from a surface. The test used to determine surface cleanliness involved the following steps:

1. A rosin flux was painted liberally onto a FR-4 test board (an epoxy printed wiring board with tracing made of tinned copper).
2. The board so treated was then heated in an oven at about 175° C. for about 1-2 minutes to activate the rosin flux.
3. The board was then immersed in solder (Sn63, a 63/37 Sn/lead solder) at about 200° C. for about 10 seconds.
4. The board was then cleaned by immersion in the boiling cleaning composition for about 3 minutes and providing gentle movement of the board. The board was then immersed in a fresh bath of cleaning composition to rinse for about 2 minutes.
5. The board was then tested for residual ionics with an Omega Meter 600 SMD ionic analyzer.

The results are given in Table 12.

TABLE 12

| Composition (wt %) | Board # | Residual Ionics (μgrams NaCl/sq in) Flux - Alpha 611F (RMA) |
|---|---|---|
| HFC-63-14mcee/ Trans-DCE/MeOH (18.7/73.2/8.1) | 1 | 14.9 |
| | 2 | 16.4 |
| | 3 | 11.4 |
| | 4 | 10.4 |
| | 5 | 10.5 |
| | AVG | 12.7 |

Example 8

Solvency Power

A measure of "solvency power"—the ability of a solvent to dissolve an organic residue—is the Kauri-Butanol value (Kb) determined by ASTM D-1133-94. The test was run by measuring 10 grams of the present composition and adding an oil/grease/fluid drop-wise until the solution becomes hazy and non-homogeneous. The point of non-homogeneity is considered to be the solubility point or saturation point for that residue in the present composition and is reported in grams residue per 100 grams of the present composition or weight percent solubility.

TABLE 13

| Components | Concentration (wt %) | Kb value |
|---|---|---|
| HFC-63-14mcee/trans-DCE/MeOH | 24.0/70.0/6.0 | 103 |
| HFC-63-14mcee/trans-DCE/MeOH | 18.7/73.2/8.1 | >164 |
| HFC-63-14mcee/trans-DCE | 20.0/80.0 | 66 |
| HFC-63-14mcee/trans-DCE | 24.0/76.0 | 59 |
| HFC-63-14mcee/$C_4F_9OCH_3$/trans-DCE | 5.0/40.0/55.0 | 46 |
| HFC-63-14mcee/$C_4F_9OC_2H_5$/trans-DCE | 13.0/17.0/70.0 | 66 |
| HFC-63-14mcee/$C_4F_9OC_2H_5$/trans-DCE/MeOH | 8/16/68/8 | >200 |

The results show good solvency power of the present compositions as demonstrated by high Kb values.

Example 9

Flammability

The flammability of the compositions of the present invention was evaluated by the Tag Closed Cup (ASTM D-56-82) test. The results are given in Table 14.

TABLE 14

| Composition | Flash point |
|---|---|
| HFC-63-14mcee/trans-DCE/MeOH (18.7 wt %/73.2 wt %/8.1 wt %) | No flash point |
| HFC-63-14mcee/trans-DCE/IPA (22.5 wt %/75.0 wt %/2.5 wt %) | No flash point |

Example 10

Impact of Vapor Leakage

A vessel is charged with an initial composition at a temperature of 50° C., and the vapor pressure of the composition is measured. The composition is allowed to leak from the vessel, while the temperature is held constant at 50° C., until 50 weight percent of the initial composition is removed, at which time the vapor pressure of the composition remaining in the vessel is measured. Mathmatically predicted results are summarized in Table 15 below.

TABLE 15

| Composition wt % | Initial Pres. (Psia) | Initial Pres. KPa | After 50% Leak Psia | After 50% Leak kPa | Delta P % |
|---|---|---|---|---|---|
| HFC-63-14mcee/trans-DCE/MeOH (50° C.) | | | | | |
| 1/94/5 | 20.05 | 138.2 | 18.60 | 128.2 | 7.2% |
| 40/59/1 | 18.04 | 124.4 | 16.75 | 115.5 | 7.2% |
| 1/69/30 | 20.03 | 138.1 | 18.38 | 126.7 | 8.2% |
| 25/55/20 | 19.81 | 136.6 | 18.42 | 127.0 | 7.0% |
| 10/70/20 | 20.11 | 138.7 | 19.70 | 135.8 | 2.0% |
| 10/80/10 | 20.16 | 139.0 | 20.11 | 138.7 | 0.2% |
| 20/75/5 | 19.74 | 136.1 | 19.27 | 132.9 | 2.4% |

TABLE 15-continued

| Composition wt % | Initial Pres. (Psia) | Initial Pres. KPa | After 50% Leak Psia | After 50% Leak kPa | Delta P % |
|---|---|---|---|---|---|
| 20/65/15 | 20.00 | 137.9 | 19.70 | 135.8 | 1.5% |
| 20/79/1 | 18.22 | 125.6 | 16.69 | 115.1 | 8.4% |
| HFC-63-14mcee/trans-DCE/EtOH (50° C.) | | | | | |
| 1/94/5 | 16.94 | 116.8 | 16.84 | 116.1 | 0.6% |
| 40/59/1 | 17.13 | 118.1 | 16.67 | 114.9 | 2.7% |
| 1/79/20 | 16.65 | 114.8 | 15.94 | 109.9 | 4.3% |
| 25/55/20 | 17.12 | 118.0 | 16.05 | 110.7 | 6.3% |
| 10/70/20 | 17.14 | 118.2 | 15.90 | 109.6 | 7.2% |
| 10/80/10 | 17.40 | 120.0 | 17.05 | 117.6 | 2.0% |
| 20/75/5 | 17.58 | 121.2 | 17.54 | 120.9 | 0.2% |
| 20/65/15 | 17.38 | 119.8 | 16.95 | 116.9 | 2.5% |
| 20/79/1 | 17.05 | 117.6 | 16.73 | 115.4 | 1.9% |
| HFC-63-14mcee/trans-DCE/IPA (50° C.) | | | | | |
| 1/94/5 | 16.24 | 112.0 | 16.19 | 111.6 | 0.3% |
| 40/59/1 | 16.58 | 114.3 | 16.47 | 113.6 | 0.7% |
| 1/79/20 | 15.71 | 108.3 | 14.92 | 102.9 | 5.0% |
| 25/55/20 | 15.82 | 109.1 | 14.38 | 99.1 | 9.1% |
| 10/70/20 | 15.95 | 110.0 | 14.91 | 102.8 | 6.5% |
| 10/80/10 | 16.42 | 113.2 | 16.13 | 111.2 | 1.8% |
| 20/75/5 | 16.68 | 115.0 | 16.65 | 114.8 | 0.2% |
| 20/65/15 | 16.21 | 111.8 | 15.61 | 107.6 | 3.7% |
| 20/79/1 | 16.63 | 114.7 | 16.60 | 114.5 | 0.2% |

Analysis of the above data shows the difference in vapor pressure between the original composition and the composition remaining after 50 weight percent has been removed is less then about 10 percent for compositions of the present invention.

Example 11

Impact of Vapor Leakage on Vapor Pressure

A vessel is charged with an initial composition at a specified temperature, and the initial vapor pressure of the composition is measured. The composition is allowed to leak from the vessel, while the temperature is held constant, until 50 weight percent of the initial composition is removed, at which time the vapor pressure of the composition remaining in the vessel is measured. Mathematically predicted results are summarized in Table 16 below.

TABLE 16

| Composition (wt % A/wt % B) | Vapor Pressure | | | | Delta P (%) |
|---|---|---|---|---|---|
| | Initial P (Psia) | Initial P (kPa) | After 50% Leak (Psia) | After 50% Leak (kPa) | |
| HFC-63-14mcee/cyclohexane (71.5° C.) | | | | | |
| 61.1/38.9 | 14.69 | 101.3 | 14.69 | 101.3 | 0.0% |
| 80/20 | 14.42 | 99.4 | 13.63 | 94.0 | 5.5% |
| 82/18 | 14.32 | 98.7 | 13.19 | 90.9 | 7.9% |
| 83/17 | 14.25 | 98.3 | 12.92 | 89.1 | 9.3% |
| 84/16 | 14.17 | 97.7 | 12.60 | 86.9 | 11.1% |
| 40/60 | 14.63 | 100.9 | 14.28 | 98.5 | 2.4% |
| 39/61 | 14.62 | 100.8 | 14.03 | 96.7 | 4.0% |
| 38/62 | 14.62 | 100.8 | 13.38 | 92.3 | 8.5% |
| HFC-63-14mcee/2,2,3-trimethylbutane (69.5° C.) | | | | | |
| 60.8/39.2 | 14.70 | 101.4 | 14.70 | 101.4 | 0.0% |
| 80/20 | 14.53 | 100.2 | 13.70 | 94.5 | 5.7% |
| 82/18 | 14.45 | 99.6 | 13.17 | 90.8 | 8.9% |
| 83/17 | 14.41 | 99.4 | 12.82 | 88.4 | 11.0% |
| 40/60 | 14.66 | 101.1 | 14.05 | 96.9 | 4.2% |
| 39/61 | 14.65 | 101.0 | 13.66 | 94.2 | 6.8% |
| 38/62 | 14.65 | 101.0 | 12.97 | 89.4 | 11.5% |
| HFC-63-14mcee/2,4-dimethylpentane (69.4° C.) | | | | | |
| 60.6/39.4 | 14.70 | 101.4 | 14.70 | 101.4 | 0.0% |
| 70/30 | 14.68 | 101.2 | 14.61 | 100.7 | 0.5% |
| 75/25 | 14.63 | 100.9 | 14.36 | 99.0 | 1.8% |
| 80/20 | 14.53 | 100.2 | 13.68 | 94.3 | 5.8% |
| 82/18 | 14.45 | 99.6 | 13.15 | 90.7 | 9.0% |
| 83/17 | 14.41 | 99.4 | 12.79 | 88.2 | 11.2% |
| 50/50 | 14.69 | 101.3 | 14.65 | 101.0 | 0.3% |
| 40/60 | 14.66 | 101.1 | 14.16 | 97.6 | 3.4% |
| 39/61 | 14.66 | 101.1 | 13.80 | 95.1 | 5.9% |
| 38/62 | 14.66 | 101.1 | 13.09 | 90.3 | 10.7% |
| HFC-63-14mcee/3,3-dimethylpentane (72.8° C.) | | | | | |
| 65.1/34.9 | 14.68 | 101.2 | 14.68 | 101.2 | 0.0% |
| 75/25 | 14.64 | 100.9 | 14.50 | 100.0 | 1.0% |
| 80/20 | 14.55 | 100.3 | 14.05 | 96.9 | 3.4% |
| 84/16 | 14.41 | 99.4 | 13.13 | 90.5 | 8.9% |
| 85/15 | 14.35 | 98.9 | 12.75 | 87.9 | 11.1% |
| 50/50 | 14.65 | 101.0 | 14.55 | 100.3 | 0.7% |
| 42/58 | 14.62 | 100.8 | 13.26 | 91.4 | 9.3% |
| HFC-63-14mcee/2,3-dimethylpentane (75.4° C.) | | | | | |
| 68.4/31.6 | 14.66 | 101.1 | 14.66 | 101.1 | 0.0% |
| 80/20 | 14.57 | 100.5 | 14.27 | 98.4 | 2.1% |
| 85/15 | 14.40 | 99.3 | 13.30 | 91.7 | 7.6% |
| 86/14 | 14.34 | 98.9 | 12.95 | 89.3 | 9.7% |
| 87/13 | 14.27 | 98.4 | 12.53 | 86.4 | 12.2% |
| 50/50 | 14.61 | 100.7 | 14.44 | 99.6 | 1.2% |
| 45/55 | 14.59 | 100.6 | 13.51 | 93.1 | 7.4% |
| 44/56 | 14.58 | 100.5 | 12.38 | 85.4 | 15.1% |
| HFC-63-14mcee/2-methylhexane (75.4° C.) | | | | | |
| 68.3/31.7 | 14.70 | 101.4 | 14.70 | 101.4 | 0.0% |
| 80/20 | 14.61 | 100.7 | 14.30 | 98.6 | 2.1% |
| 85/15 | 14.44 | 99.6 | 13.33 | 91.9 | 7.7% |
| 86/14 | 14.38 | 99.1 | 12.97 | 89.4 | 9.8% |
| 50/50 | 14.65 | 101.0 | 14.48 | 99.8 | 1.2% |
| 45/55 | 14.63 | 100.9 | 13.58 | 93.6 | 7.2% |
| 44/56 | 14.62 | 100.8 | 12.50 | 86.2 | 14.5% |
| HFC-63-14mcee/3-methylhexane (76.4° C.) | | | | | |
| 69.6/30.4 | 14.69 | 101.3 | 14.69 | 101.3 | 0.0% |
| 80/20 | 14.61 | 100.7 | 14.37 | 99.1 | 1.6% |
| 86/14 | 14.40 | 99.3 | 13.20 | 91.0 | 8.3% |
| 87/13 | 14.33 | 98.8 | 12.82 | 88.4 | 10.5% |
| 50/50 | 14.62 | 100.8 | 14.41 | 99.4 | 1.4% |
| 46/55 | 14.60 | 100.7 | 13.49 | 93.0 | 7.6% |
| 45/55 | 14.60 | 100.7 | 12.25 | 84.5 | 16.1% |
| HFC-63-14mcee/n-heptane (80.5° C.) | | | | | |
| 74.9/25.1 | 14.71 | 101.4 | 14.71 | 101.4 | 0.0% |
| 85/15 | 14.58 | 100.5 | 14.18 | 97.8 | 2.7% |
| 89/11 | 14.35 | 98.9 | 13.14 | 90.6 | 8.4% |
| 90/10 | 14.25 | 98.3 | 12.72 | 87.7 | 10.7% |
| 60/40 | 14.64 | 100.9 | 14.51 | 100.0 | 0.9% |
| 55/45 | 14.61 | 100.7 | 14.38 | 99.1 | 1.6% |
| 51/49 | 14.58 | 100.5 | 13.80 | 95.1 | 5.3% |
| 50/50 | 14.58 | 100.5 | 13.02 | 89.8 | 10.7% |
| HFC-63-14mcee/methylcyclohexane (80.4° C.) | | | | | |
| 73.2/26.8 | 14.71 | 101.4 | 14.71 | 101.4 | 0.0% |
| 85/15 | 14.52 | 100.1 | 14.00 | 96.5 | 3.6% |
| 88/12 | 14.32 | 98.7 | 13.25 | 91.4 | 7.5% |
| 89/11 | 14.23 | 98.1 | 12.91 | 89.0 | 9.3% |
| 60/40 | 14.65 | 101.0 | 14.54 | 100.3 | 0.8% |
| 50/50 | 14.58 | 100.5 | 14.33 | 98.8 | 1.7% |
| 48/52 | 14.57 | 100.5 | 13.91 | 95.9 | 4.5% |

TABLE 16-continued

Vapor Pressure

| Composition (wt % A/wt % B) | Initial P (Psia) | Initial P (kPa) | After 50% Leak (Psia) | After 50% Leak (kPa) | Delta P (%) |
|---|---|---|---|---|---|
| HFC-63-14mcee/toluene (87.2° C.) | | | | | |
| 83.8/16.2 | 14.68 | 101.2 | 14.68 | 101.2 | 0.0% |
| 90/10 | 14.55 | 100.3 | 14.32 | 98.7 | 1.6% |
| 95/5 | 13.95 | 96.2 | 12.99 | 89.6 | 6.9% |
| 97/3 | 13.33 | 91.9 | 12.22 | 84.3 | 8.3% |
| 98/2 | 12.86 | 88.7 | 11.86 | 81.8 | 7.8% |
| 99/1 | 12.22 | 84.3 | 11.56 | 79.7 | 5.4% |
| 70/30 | 14.52 | 100.1 | 14.28 | 98.5 | 1.7% |
| 60/40 | 14.37 | 99.1 | 13.47 | 92.9 | 6.3% |
| 59/41 | 14.36 | 99.0 | 13.10 | 90.3 | 8.8% |
| HFC-63-14mcee/isooctane (78.9° C.) | | | | | |
| 72.9/27.1 | 14.69 | 101.3 | 14.69 | 101.3 | 0.0% |
| 80/20 | 14.66 | 101.1 | 14.55 | 100.3 | 0.8% |
| 88/12 | 14.42 | 99.4 | 13.00 | 89.6 | 9.8% |
| 60/40 | 14.65 | 101.0 | 14.59 | 100.6 | 0.4% |
| 50/50 | 14.61 | 100.7 | 14.14 | 97.5 | 3.2% |
| 49/51 | 14.61 | 100.7 | 13.80 | 95.1 | 5.5% |
| 48/52 | 14.61 | 100.7 | 12.90 | 88.9 | 11.7% |
| HFC-63-14mcee/n-octane (90.0° C.) | | | | | |
| 88.4/11.6 | 14.69 | 101.3 | 14.69 | 101.3 | 0.0% |
| 95/5 | 14.43 | 99.5 | 13.93 | 96.0 | 3.5% |
| 99/1 | 13.20 | 91.0 | 12.60 | 86.9 | 4.5% |
| 70/30 | 14.46 | 99.7 | 14.20 | 97.9 | 1.8% |
| 63/37 | 14.38 | 99.1 | 13.71 | 94.5 | 4.7% |
| 62/38 | 14.37 | 99.1 | 13.13 | 90.5 | 8.6% |
| HFC-63-14mcee/2-bromopropane (56.8° C.) | | | | | |
| 33.6/66.4 | 14.70 | 101.4 | 14.70 | 101.4 | 0.0% |
| 20/80 | 14.63 | 100.9 | 14.38 | 99.1 | 1.7% |
| 10/90 | 14.35 | 98.9 | 13.62 | 93.9 | 5.1% |
| 1/99 | 13.49 | 93.0 | 13.32 | 91.8 | 1.3% |
| 50/50 | 14.64 | 100.9 | 14.50 | 100.0 | 1.0% |
| 68/32 | 14.32 | 98.7 | 13.00 | 89.6 | 9.2% |
| 69/31 | 14.29 | 98.5 | 12.79 | 88.2 | 10.5% |
| HFC-63-14mcee/1-bromopropane (66.3° C.) | | | | | |
| 46.0/54.0 | 14.70 | 101.4 | 14.70 | 101.4 | 0.0% |
| 30/70 | 14.62 | 100.8 | 14.28 | 98.5 | 2.3% |
| 20/80 | 14.42 | 99.4 | 13.12 | 90.5 | 9.0% |
| 19/81 | 14.39 | 99.2 | 13.01 | 89.7 | 9.6% |
| 18/82 | 14.36 | 99.0 | 12.90 | 88.9 | 10.2% |
| 60/40 | 14.64 | 100.9 | 14.49 | 99.9 | 1.0% |
| 70/30 | 14.46 | 99.7 | 13.72 | 94.6 | 5.1% |
| 74/26 | 14.32 | 98.7 | 13.02 | 89.8 | 9.1% |
| 75/25 | 14.28 | 98.5 | 12.79 | 88.2 | 10.4% |
| HFC-63-14mcee/1,2-dichloroethane (74.5° C.) | | | | | |
| 59.4/40.6 | 14.70 | 101.4 | 14.70 | 101.4 | 0.0% |
| 70/30 | 14.63 | 100.9 | 14.48 | 99.8 | 1.0% |
| 80/20 | 14.31 | 98.7 | 13.35 | 92.0 | 6.7% |
| 82/18 | 14.17 | 97.7 | 12.89 | 88.9 | 9.0% |
| 83/17 | 14.09 | 97.1 | 12.62 | 87.0 | 10.4% |
| 40/60 | 14.62 | 100.8 | 14.39 | 99.2 | 1.6% |
| 36/64 | 14.59 | 100.6 | 13.72 | 94.6 | 6.0% |
| 35/65 | 14.58 | 100.5 | 12.97 | 89.4 | 11.0% |
| HFC-63-14mcee/1,1-dichloroethane (56.4° C.) | | | | | |
| 20.7/79.3 | 14.70 | 101.4 | 14.70 | 101.4 | 0.0% |
| 10/90 | 14.64 | 100.9 | 14.56 | 100.4 | 0.5% |
| 1/99 | 14.34 | 98.9 | 14.29 | 98.5 | 0.3% |
| 30/70 | 14.67 | 101.1 | 14.63 | 100.9 | 0.3% |
| 40/60 | 14.58 | 100.5 | 14.40 | 99.3 | 1.2% |
| 50/50 | 14.40 | 99.3 | 13.90 | 95.8 | 3.5% |
| 60/40 | 14.07 | 97.0 | 12.92 | 89.1 | 8.2% |
| 62/38 | 13.97 | 96.3 | 12.63 | 87.1 | 9.6% |
| HFC-63-14mcee/fluorobenzene (75.1° C.) | | | | | |
| 64.6/35.4 | 14.70 | 101.4 | 14.70 | 101.4 | 0.0% |
| 80/20 | 14.50 | 100.0 | 13.96 | 96.3 | 3.7% |
| 85/15 | 14.22 | 98.0 | 12.81 | 88.3 | 9.9% |
| 50/50 | 14.62 | 100.8 | 14.38 | 99.1 | 1.6% |
| 40/60 | 14.49 | 99.9 | 13.25 | 91.4 | 8.6% |
| 39/61 | 14.47 | 99.8 | 13.07 | 90.1 | 9.7% |
| HFC-63-14mcee/methylene bromide (86.0° C.) | | | | | |
| 64.9/35.1 | 14.68 | 101.2 | 14.68 | 101.2 | 0.0% |
| 80/20 | 14.39 | 99.2 | 14.01 | 96.6 | 2.6% |
| 85/15 | 14.06 | 96.9 | 13.36 | 92.1 | 5.0% |
| 90/10 | 13.49 | 93.0 | 12.51 | 86.3 | 7.3% |
| 95/5 | 12.53 | 86.4 | 11.60 | 80.0 | 7.4% |
| 99/1 | 11.30 | 77.9 | 11.01 | 75.9 | 2.6% |
| 50/50 | 14.56 | 100.4 | 14.36 | 99.0 | 1.4% |
| 40/60 | 14.38 | 99.1 | 13.67 | 94.3 | 4.9% |
| 37/63 | 14.32 | 98.7 | 13.18 | 90.9 | 8.0% |
| 36/64 | 14.30 | 98.6 | 12.95 | 89.3 | 9.4% |
| HFC-63-14mcee/trichloroethylene (77.0° C.) | | | | | |
| 59.7/40.3 | 14.70 | 101.4 | 14.70 | 101.4 | 0.0% |
| 70/30 | 14.64 | 100.9 | 14.49 | 99.9 | 1.0% |
| 80/20 | 14.33 | 98.8 | 13.32 | 91.8 | 7.0% |
| 82/18 | 14.12 | 97.4 | 12.56 | 86.6 | 11.0% |
| 83/17 | 14.20 | 97.9 | 12.84 | 88.5 | 9.6% |
| 40/60 | 14.57 | 100.5 | 14.01 | 96.6 | 3.8% |
| 35/65 | 14.49 | 99.9 | 13.22 | 91.1 | 8.8% |
| 34/66 | 14.47 | 99.8 | 13.01 | 89.7 | 10.1% |
| HFC-63-14mcee/tetrachloroethylene (91.4° C.) | | | | | |
| 82.6/17.4 | 14.70 | 101.4 | 14.70 | 101.4 | 0.0% |
| 90/10 | 14.38 | 99.1 | 14.23 | 98.1 | 1.0% |
| 95/5 | 14.10 | 97.2 | 13.76 | 94.9 | 2.4% |
| 99/1 | 13.28 | 91.6 | 13.11 | 90.4 | 1.3% |
| 70/30 | 14.52 | 100.1 | 14.30 | 98.6 | 1.5% |
| 60/40 | 14.28 | 98.5 | 13.67 | 94.3 | 4.3% |
| 55/45 | 14.16 | 97.6 | 13.10 | 90.3 | 7.5% |
| 53/47 | 14.10 | 97.2 | 12.74 | 87.8 | 9.6% |
| HFC-63-14mcee/chlorobenzene (94.1° C.) | | | | | |
| 93.6/6.4 | 14.68 | 101.2 | 14.68 | 101.2 | 0.0% |
| 99/1 | 14.63 | 100.9 | 14.61 | 100.7 | 0.1% |
| 80/20 | 14.33 | 98.8 | 14.28 | 98.5 | 0.3% |
| 75/25 | 14.18 | 97.8 | 13.71 | 94.5 | 3.3% |
| 70/30 | 13.77 | 94.9 | 12.54 | 86.5 | 8.9% |
| 69/31 | 13.73 | 94.7 | 12.34 | 85.1 | 10.1% |
| HFC-63-14mcee/cis-1,2-dichloroethylene (58.2° C.) | | | | | |
| 37.0/63.0 | 14.71 | 101.4 | 14.71 | 101.4 | 0.0% |
| 20/80 | 14.58 | 100.5 | 14.35 | 98.9 | 1.6% |
| 10/90 | 14.29 | 98.5 | 13.91 | 95.9 | 2.7% |
| 1/99 | 13.73 | 94.7 | 13.66 | 94.2 | 0.5% |
| 50/50 | 14.65 | 101.0 | 14.57 | 100.5 | 0.5% |
| 70/30 | 14.3 | 98.6 | 13.29 | 91.6 | 7.1% |
| 72/28 | 14.22 | 98.0 | 12.94 | 89.2 | 9.0% |
| 73/37 | 14.18 | 97.8 | 12.74 | 87.8 | 10.2% |
| HFC-63-14mcee/methanol (65.5° C.) | | | | | |
| 47.0/53.0 | 14.67 | 101.1 | 14.67 | 101.1 | 0.0% |
| 20/80 | 14.65 | 101.0 | 14.64 | 100.9 | 0.1% |
| 10/90 | 14.63 | 100.9 | 14.63 | 100.9 | 0.0% |
| 1/99 | 14.61 | 100.7 | 14.61 | 100.7 | 0.0% |
| 70/30 | 14.58 | 100.5 | 14.55 | 100.3 | 0.2% |
| 80/20 | 14.37 | 99.1 | 14.21 | 98.0 | 1.1% |
| 90/10 | 13.72 | 94.6 | 13.06 | 90.0 | 4.8% |
| 93/7 | 13.30 | 91.7 | 12.16 | 83.8 | 8.6% |
| 94/6 | 13.11 | 90.4 | 11.61 | 80.0 | 11.4% |
| HFC-63-14mcee/ethanol (71.3° C.) | | | | | |
| 79.4/20.6 | 14.68 | 101.2 | 14.68 | 101.2 | 0.0% |
| 90/10 | 14.53 | 100.2 | 13.98 | 96.4 | 3.8% |
| 92/8 | 14.40 | 99.3 | 13.10 | 90.3 | 9.0% |
| 60/40 | 14.48 | 99.8 | 13.39 | 92.3 | 7.5% |

TABLE 16-continued

| Composition (wt % A/wt % B) | Initial P (Psia) | Initial P (kPa) | After 50% Leak (Psia) | After 50% Leak (kPa) | Delta P (%) |
|---|---|---|---|---|---|
| 58/42 | 14.44 | 99.6 | 13.08 | 90.2 | 9.4% |
| 57/43 | 14.42 | 99.4 | 12.92 | 89.1 | 10.4% |
| HFC-63-14mcee/n-propanol (82.3° C.) | | | | | |
| 86.5/13.5 | 14.72 | 101.5 | 14.72 | 101.5 | 0.0% |
| 94/6 | 14.47 | 99.8 | 13.50 | 93.1 | 6.7% |
| 95/5 | 14.33 | 98.8 | 12.76 | 88.0 | 11.0% |
| 70/30 | 14.55 | 100.3 | 13.40 | 92.4 | 7.9% |
| 69/31 | 14.54 | 100.3 | 13.09 | 90.3 | 10.0% |
| HFC-63-14mcee/2-methyl-2-propanol (71.8° C.) | | | | | |
| 73.3/26.7 | 14.72 | 101.5 | 14.72 | 101.5 | 0.0% |
| 87/13 | 14.60 | 100.7 | 13.91 | 95.9 | 4.7% |
| 88/12 | 14.56 | 100.4 | 13.57 | 93.6 | 6.8% |
| 89/11 | 14.52 | 100.1 | 13.06 | 90.0 | 10.1% |
| 52/48 | 14.60 | 100.7 | 13.26 | 91.4 | 9.2% |
| 50/50 | 14.59 | 100.6 | 12.67 | 87.4 | 13.2% |
| HFC-63-14mcee/2-methyl-2-butanol (82.1° C.) | | | | | |
| 82.9/17.1 | 14.68 | 101.2 | 14.68 | 101.2 | 0.0% |
| 90/10 | 14.60 | 100.7 | 14.25 | 98.3 | 2.4% |
| 92/8 | 14.50 | 100.0 | 13.56 | 93.5 | 6.5% |
| 93/7 | 14.43 | 99.5 | 12.93 | 89.1 | 10.4% |
| 70/30 | 14.62 | 100.8 | 14.39 | 99.2 | 1.6% |
| 65/35 | 14.58 | 100.5 | 13.84 | 95.4 | 5.1% |
| 63/37 | 14.56 | 100.4 | 13.32 | 91.8 | 8.5% |
| 62/38 | 14.55 | 100.3 | 12.94 | 89.2 | 11.1% |
| HFC-63-14mcee/2-butanol (81.0° C.) | | | | | |
| 83.3/16.7 | 14.71 | 101.4 | 14.71 | 101.4 | 0.0% |
| 90/10 | 14.63 | 100.9 | 14.32 | 98.7 | 2.1% |
| 93/7 | 14.45 | 99.6 | 13.11 | 90.4 | 9.3% |
| 70/30 | 14.63 | 100.9 | 14.31 | 98.7 | 2.2% |
| 64/36 | 14.57 | 100.5 | 13.21 | 91.1 | 9.3% |
| 63/37 | 14.56 | 100.4 | 12.82 | 88.4 | 12.0% |
| HFC-63-14mcee/isobutanol (85.5° C.) | | | | | |
| 87.8/12.2 | 14.72 | 101.5 | 14.72 | 101.5 | 0.0% |
| 95/5 | 14.42 | 99.4 | 13.36 | 92.1 | 7.4% |
| 96/4 | 14.23 | 98.1 | 12.62 | 87.0 | 11.3% |
| 70/30 | 14.53 | 100.2 | 13.30 | 91.7 | 8.5% |
| 69/31 | 14.52 | 100.1 | 12.91 | 89.0 | 11.1% |
| HFC-63-14mcee/n-butanol (89.4° C.) | | | | | |
| 91.7/8.3 | 14.72 | 101.5 | 14.72 | 101.5 | 0.0% |
| 95/5 | 14.63 | 100.9 | 14.42 | 99.4 | 1.4% |
| 99/1 | 13.39 | 92.3 | 12.48 | 86.0 | 6.8% |
| 80/20 | 14.53 | 100.2 | 14.14 | 97.5 | 2.7% |
| 75/25 | 14.43 | 99.5 | 13.24 | 91.3 | 8.2% |
| 74/26 | 14.41 | 99.4 | 12.86 | 88.7 | 10.8% |
| HFC-63-14mcee/2-methoxyethanol (89.0° C.) | | | | | |
| 93.4/6.6 | 14.69 | 101.3 | 14.69 | 101.3 | 0.0% |
| 97/3 | 14.58 | 100.5 | 13.88 | 95.7 | 4.8% |
| 98/2 | 14.41 | 99.4 | 12.75 | 87.9 | 11.5% |
| 80/20 | 14.6 | 100.7 | 14.21 | 98.0 | 2.7% |
| 77/23 | 14.58 | 100.5 | 13.42 | 92.5 | 8.0% |
| 76/24 | 14.57 | 100.5 | 12.80 | 88.3 | 12.1% |
| HFC-63-14mcee/2,2-dimethyl-1,3-dioxolane (76.2° C.) | | | | | |
| 72.2/27.8 | 14.7 | 101.4 | 14.70 | 101.4 | 0.0% |
| 80/20 | 14.67 | 101.1 | 14.57 | 100.5 | 0.7% |
| 85/15 | 14.59 | 100.6 | 13.99 | 96.5 | 4.1% |
| 87/13 | 14.51 | 100.0 | 13.37 | 92.2 | 7.9% |
| 88/12 | 14.46 | 99.7 | 12.90 | 88.9 | 10.8% |
| 60/40 | 14.67 | 101.1 | 14.58 | 100.5 | 0.6% |
| 51/49 | 14.63 | 100.9 | 13.77 | 94.9 | 5.9% |
| 50/50 | 14.62 | 100.8 | 13.46 | 92.8 | 7.9% |
| HFC-63-14mcee/acetonitrile (75.1° C.) | | | | | |
| 73.6/26.4 | 14.71 | 101.4 | 14.71 | 101.4 | 0.0% |
| 85/15 | 14.53 | 100.2 | 14.19 | 97.8 | 2.3% |
| 91/9 | 13.95 | 96.2 | 12.66 | 87.3 | 9.2% |
| 92/8 | 13.75 | 94.8 | 12.20 | 84.1 | 11.3% |
| 60/40 | 14.63 | 100.9 | 14.44 | 99.6 | 1.3% |
| 50/50 | 14.53 | 100.2 | 13.62 | 93.9 | 6.3% |
| 46/54 | 14.47 | 99.8 | 13.06 | 90.0 | 9.7% |
| 45/55 | 14.45 | 99.6 | 12.92 | 89.1 | 10.6% |
| HFC-63-14mcee/propionitrile (83.9° C.) | | | | | |
| 83.0/17.0 | 14.68 | 101.2 | 14.68 | 101.2 | 0.0% |
| 90/10 | 14.51 | 100.0 | 14.24 | 98.2 | 1.9% |
| 95/5 | 13.75 | 94.8 | 12.62 | 87.0 | 8.2% |
| 96/4 | 13.41 | 92.5 | 12.10 | 83.4 | 9.8% |
| 97/3 | 12.95 | 89.3 | 11.55 | 79.6 | 10.8% |
| 70/30 | 14.53 | 100.2 | 14.21 | 98.0 | 2.2% |
| 61/39 | 14.36 | 99.0 | 13.00 | 89.6 | 9.5% |
| 60/40 | 14.34 | 98.9 | 12.74 | 87.8 | 11.2% |
| HFC-63-14mcee/butyronitrile (91.2° C.) | | | | | |
| 90.9/9.1 | 14.72 | 101.5 | 14.72 | 101.5 | 0.0% |
| 95/5 | 14.55 | 100.3 | 14.41 | 99.4 | 1.0% |
| 99/1 | 13.52 | 93.2 | 13.24 | 91.3 | 2.1% |
| 80/20 | 14.42 | 99.4 | 14.05 | 96.9 | 2.6% |
| 71/29 | 14.12 | 97.4 | 12.83 | 88.5 | 9.1% |
| 70/30 | 14.08 | 97.1 | 12.56 | 86.6 | 10.8% |
| HFC-63-14mcee/nitromethane (90.0° C.) | | | | | |
| 81.0/19.0 | 14.7 | 101.4 | 14.70 | 101.4 | 0.0% |
| 90/10 | 14.45 | 99.6 | 14.33 | 98.8 | 0.8% |
| 95/5 | 13.87 | 95.6 | 13.62 | 93.9 | 1.8% |
| 99/1 | 12.81 | 88.3 | 12.68 | 87.4 | 1.0% |
| 70/30 | 14.56 | 100.4 | 14.44 | 99.6 | 0.8% |
| 60/40 | 14.35 | 98.9 | 14.01 | 96.6 | 2.4% |
| 50/50 | 14.15 | 97.6 | 13.57 | 93.6 | 4.1% |
| 47/53 | 14.09 | 97.1 | 13.43 | 92.6 | 4.7% |
| HFC-63-14mcee/n-methylmorpholine (89.6° C.) | | | | | |
| 86.3/13.7 | 14.69 | 101.3 | 14.69 | 101.3 | 0.0% |
| 95/5 | 14.21 | 98.0 | 13.69 | 94.4 | 3.7% |
| 97/3 | 13.75 | 94.8 | 13.08 | 90.2 | 4.9% |
| 99/1 | 12.91 | 89.0 | 12.48 | 86.0 | 3.3% |
| 70/30 | 14.41 | 99.4 | 13.89 | 95.8 | 3.6% |
| 64/36 | 14.26 | 98.3 | 13.03 | 89.8 | 8.6% |
| 63/37 | 14.23 | 98.1 | 12.79 | 88.2 | 10.1% |
| HFC-63-14mcee/morpholine (94.5° C.) | | | | | |
| 95.6/4.4 | 14.7 | 101.4 | 14.70 | 101.4 | 0.0% |
| 99/1 | 14.49 | 99.9 | 14.46 | 99.7 | 0.2% |
| 80/20 | 13.93 | 96.0 | 13.23 | 91.2 | 5.0% |
| 75/25 | 13.68 | 94.3 | 12.57 | 86.7 | 8.1% |
| 74/26 | 13.63 | 94.0 | 12.40 | 85.5 | 9.0% |
| 73/27 | 13.58 | 93.6 | 12.20 | 84.1 | 10.2% |
| HFC-63-14mcee/1,2-dimethoxyethane (71.6° C.) | | | | | |
| 67.6/36.4 | 14.68 | 101.2 | 14.68 | 101.2 | 0.0% |
| 80/20 | 14.61 | 100.7 | 14.34 | 98.9 | 1.8% |
| 85/15 | 14.48 | 99.8 | 13.37 | 92.2 | 7.7% |
| 86/14 | 14.44 | 99.6 | 12.98 | 89.5 | 10.1% |
| 50/50 | 14.64 | 100.9 | 14.36 | 99.0 | 1.9% |
| 45/55 | 14.62 | 100.8 | 13.16 | 90.7 | 10.0% |
| HFC-63-14mcee/ethyl acetate (70.3° C.) | | | | | |
| 60.6/39.4 | 14.68 | 101.2 | 14.68 | 101.2 | 0.0% |
| 70/30 | 14.64 | 100.9 | 14.55 | 100.3 | 0.6% |
| 80/20 | 14.43 | 99.5 | 13.66 | 94.2 | 5.3% |
| 83/17 | 14.28 | 98.5 | 12.92 | 89.1 | 9.5% |
| 50/50 | 14.65 | 101.0 | 14.54 | 100.3 | 0.8% |
| 40/60 | 14.55 | 100.3 | 13.89 | 95.8 | 4.5% |
| 35/65 | 14.46 | 99.7 | 13.24 | 91.3 | 8.4% |
| 34/66 | 14.44 | 99.6 | 13.09 | 90.3 | 9.3% |
| HFC-63-14mcee/methyl propionate (70.3° C.) | | | | | |
| 61.6/38.4 | 14.7 | 101.4 | 14.70 | 101.4 | 0.0% |
| 70/30 | 14.67 | 101.1 | 14.59 | 100.6 | 0.5% |
| 80/20 | 14.46 | 99.7 | 13.75 | 94.8 | 4.9% |

TABLE 16-continued

| Composition (wt % A/wt % B) | Initial P (Psia) | Initial P (kPa) | After 50% Leak (Psia) | After 50% Leak (kPa) | Delta P (%) |
|---|---|---|---|---|---|
| 83/17 | 14.31 | 98.7 | 13.06 | 90.0 | 8.7% |
| 84/16 | 14.25 | 98.3 | 12.74 | 87.8 | 10.6% |
| 50/50 | 14.65 | 101.0 | 14.52 | 100.1 | 0.9% |
| 40/60 | 14.55 | 100.3 | 13.77 | 94.9 | 5.4% |
| 35/65 | 14.46 | 99.7 | 13.06 | 90.0 | 9.7% |
| 34/66 | 14.44 | 99.6 | 12.91 | 89.0 | 10.6% |
| HFC-63-14mcee/n-propyl formate (72.9° C.) | | | | | |
| 64.0/36.0 | 14.72 | 101.5 | 14.72 | 101.5 | 0.0% |
| 80/20 | 14.53 | 100.2 | 13.98 | 96.4 | 3.8% |
| 84/16 | 14.33 | 98.8 | 13.11 | 90.4 | 8.5% |
| 85/15 | 14.26 | 98.3 | 12.78 | 88.1 | 10.4% |
| 50/50 | 14.65 | 101.0 | 14.43 | 99.5 | 1.5% |
| 40/60 | 14.52 | 100.1 | 13.41 | 92.5 | 7.6% |
| 38/62 | 14.49 | 99.9 | 13.09 | 90.3 | 9.7% |
| HFC-63-14mcee/dimethyl carbonate (79.7° C.) | | | | | |
| 71.1/28.9 | 14.68 | 101.2 | 14.68 | 101.2 | 0.0% |
| 80/20 | 14.59 | 100.6 | 14.41 | 99.4 | 1.2% |
| 89/11 | 14.03 | 96.7 | 12.62 | 87.0 | 10.0% |
| 60/40 | 14.62 | 100.8 | 14.48 | 99.8 | 1.0% |
| 50/50 | 14.50 | 100.0 | 13.77 | 94.9 | 5.0% |
| 46/54 | 14.43 | 99.5 | 13.06 | 90.0 | 9.5% |
| HFC-63-14mcee/isopropyl acetate (76.9° C.) | | | | | |
| 68.3/31.7 | 14.68 | 101.2 | 14.68 | 101.2 | 0.0% |
| 80/20 | 14.57 | 100.5 | 14.25 | 98.3 | 2.2% |
| 85/15 | 14.36 | 99.0 | 13.34 | 92.0 | 7.1% |
| 86/14 | 14.30 | 98.6 | 13.03 | 89.8 | 8.9% |
| 87/13 | 14.22 | 98.0 | 12.66 | 87.3 | 11.0% |
| 50/50 | 14.55 | 100.3 | 14.02 | 96.7 | 3.6% |
| 44/56 | 14.45 | 99.6 | 13.15 | 90.7 | 9.0% |
| 43/57 | 14.43 | 99.5 | 12.95 | 89.3 | 10.3% |
| HFC-63-14mcee/isobutyl formate (82.9° C.) | | | | | |
| 76.5/23.5 | 14.69 | 101.3 | 14.69 | 101.3 | 0.0% |
| 90/10 | 14.26 | 98.3 | 13.23 | 91.2 | 7.2% |
| 91/9 | 14.15 | 97.6 | 12.87 | 88.7 | 9.0% |
| 92/8 | 14.00 | 96.5 | 12.46 | 85.9 | 11.0% |
| 60/40 | 14.54 | 100.3 | 14.10 | 97.2 | 3.0% |
| 53/47 | 14.42 | 99.4 | 13.06 | 90.0 | 9.4% |
| HFC-63-14mcee/ethyl propionate (83.0° C.) | | | | | |
| 76.6/23.4 | 14.68 | 101.2 | 14.68 | 101.2 | 0.0% |
| 90/10 | 14.26 | 98.3 | 13.24 | 91.3 | 7.2% |
| 91/9 | 14.14 | 97.5 | 12.89 | 88.9 | 8.8% |
| 92/8 | 14 | 96.5 | 12.48 | 86.0 | 10.9% |
| 60/40 | 14.53 | 100.2 | 14.08 | 97.1 | 3.1% |
| 53/47 | 14.41 | 99.4 | 13.03 | 89.8 | 9.6% |
| HFC-63-14mcee/n-propyl acetate (84.2° C.) | | | | | |
| 78.3/21.7 | 14.7 | 101.4 | 14.70 | 101.4 | 0.0% |
| 90/10 | 14.35 | 98.9 | 13.58 | 93.6 | 5.4% |
| 92/8 | 14.12 | 97.4 | 12.91 | 89.0 | 8.6% |
| 93/7 | 13.96 | 96.3 | 12.51 | 86.3 | 10.4% |
| 60/40 | 14.51 | 100.0 | 13.90 | 95.8 | 4.2% |
| 55/45 | 14.42 | 99.4 | 13.06 | 90.0 | 9.4% |
| HFC-63-14mcee/methyl n-butyrate (84.7° C.) | | | | | |
| 79.0/21.0 | 14.68 | 101.2 | 14.68 | 101.2 | 0.0% |
| 90/10 | 14.36 | 99.0 | 13.68 | 94.3 | 4.7% |
| 93/7 | 13.98 | 96.4 | 12.68 | 87.4 | 9.3% |
| 94/6 | 13.78 | 95.0 | 12.27 | 84.6 | 11.0% |
| 60/40 | 14.47 | 99.8 | 13.78 | 95.0 | 4.8% |
| 56/44 | 14.39 | 99.2 | 13.10 | 90.3 | 9.0% |
| 55/45 | 14.37 | 99.1 | 12.86 | 88.7 | 10.5% |
| HFC-63-14mcee/butyl formate (86.9° C.) | | | | | |
| 82.2/17.8 | 14.72 | 101.5 | 14.72 | 101.5 | 0.0% |
| 90/10 | 14.53 | 100.2 | 14.19 | 97.8 | 2.3% |
| 95/5 | 13.86 | 95.6 | 12.73 | 87.8 | 8.2% |
| 99/1 | 12.10 | 83.4 | 11.41 | 78.7 | 5.7% |
| 70/30 | 14.58 | 100.5 | 14.33 | 98.8 | 1.7% |
| 59/41 | 14.37 | 99.1 | 12.97 | 89.4 | 9.7% |
| HFC-63-14mcee/diethyl carbonate (93.1° C.) | | | | | |
| 91.5/8.5 | 14.72 | 101.5 | 14.72 | 101.5 | 0.0% |
| 95/5 | 14.63 | 100.9 | 14.56 | 100.4 | 0.5% |
| 99/1 | 14.02 | 96.7 | 13.89 | 95.8 | 0.9% |
| 80/20 | 14.42 | 99.4 | 14.09 | 97.1 | 2.3% |
| 70/30 | 14.09 | 97.1 | 13.06 | 90.0 | 7.3% |
| 68/32 | 14.03 | 96.7 | 12.68 | 87.4 | 9.6% |
| HFC-63-14mcee/2-butanone (96.0° C.) | | | | | |
| 94.5/5.5 | 14.69 | 101.3 | 14.69 | 101.3 | 0.0% |
| 99/1 | 14.87 | 102.5 | 14.87 | 102.5 | 0.0% |
| 80/20 | 15.91 | 109.7 | 15.43 | 106.4 | 3.0% |
| 70/30 | 17.41 | 120.0 | 16.34 | 112.7 | 6.1% |
| 60/40 | 19.10 | 131.7 | 17.44 | 120.2 | 8.7% |
| 50/50 | 20.59 | 142.0 | 18.70 | 128.9 | 9.2% |
| 40/60 | 21.82 | 150.4 | 20.08 | 138.4 | 8.0% |
| 20/80 | 23.44 | 161.6 | 22.71 | 156.6 | 3.1% |
| 1/99 | 24.13 | 166.4 | 24.12 | 166.3 | 0.0% |
| HFC-63-14mcee/3-methyl-2-butanone (99.9° C.) | | | | | |
| 78.0/22.0 | 14.70 | 101.4 | 14.70 | 101.4 | 0.0% |
| 90/10 | 15.21 | 104.9 | 15.08 | 104.0 | 0.9% |
| 95/5 | 15.85 | 109.3 | 15.68 | 108.1 | 1.1% |
| 99/1 | 16.63 | 114.7 | 16.57 | 114.2 | 0.4% |
| 60/40 | 15.26 | 105.2 | 15.06 | 103.8 | 1.3% |
| 50/50 | 15.78 | 108.8 | 15.45 | 106.5 | 2.1% |
| 40/60 | 16.28 | 112.2 | 15.91 | 109.7 | 2.3% |
| 30/70 | 16.68 | 115.0 | 16.39 | 113.0 | 1.7% |
| 20/80 | 16.97 | 117.0 | 16.81 | 115.9 | 0.9% |
| 1/99 | 17.20 | 118.6 | 17.20 | 118.6 | 0.0% |
| HFC-63-14mcee/2,2,2-trifluoroethanol (73.3° C.) | | | | | |
| 62.0/38.0 | 14.70 | 101.4 | 14.70 | 101.4 | 0.0% |
| 70/30 | 14.66 | 101.1 | 14.59 | 100.6 | 0.5% |
| 80/20 | 14.45 | 99.6 | 13.91 | 95.9 | 3.7% |
| 84/16 | 14.20 | 97.9 | 13.08 | 90.2 | 7.9% |
| 85/15 | 14.27 | 98.4 | 12.74 | 87.8 | 10.7% |
| 40/60 | 14.42 | 99.4 | 13.96 | 96.3 | 3.2% |
| 30/70 | 14.10 | 97.2 | 13.34 | 92.0 | 5.4% |
| 20/80 | 13.64 | 94.0 | 12.82 | 88.4 | 6.0% |
| 10/90 | 13.03 | 89.8 | 12.47 | 86.0 | 4.3% |
| 1/99 | 12.35 | 85.2 | 12.28 | 84.7 | 0.6% |
| HFC-63-14mcee/2,2,3,3,3-pentafluoro-1-propanol (76.9° C.) | | | | | |
| 57.0/43.0 | 14.71 | 101.4 | 14.71 | 101.4 | 0.0% |
| 70/30 | 14.60 | 100.7 | 14.41 | 99.4 | 1.3% |
| 80/20 | 14.27 | 98.4 | 13.26 | 91.4 | 7.1% |
| 82/18 | 14.15 | 97.6 | 12.76 | 88.0 | 9.8% |
| 83/17 | 14.09 | 97.1 | 12.45 | 85.8 | 11.6% |
| 40/60 | 14.53 | 100.2 | 14.25 | 98.3 | 1.9% |
| 30/70 | 14.22 | 98.0 | 13.61 | 93.8 | 4.3% |
| 20/80 | 13.74 | 94.7 | 12.93 | 89.1 | 5.9% |
| 10/90 | 13.04 | 89.9 | 12.40 | 85.5 | 4.9% |
| 1/99 | 12.18 | 84.0 | 12.10 | 83.4 | 0.7% |
| HFC-63-14mcee/2,2,3,3-tetrafluoro-1-propanol (92.2° C.) | | | | | |
| 87.4/12.6 | 14.71 | 101.4 | 14.71 | 101.4 | 0.0% |
| 95/5 | 14.43 | 99.5 | 14.28 | 98.5 | 1.0% |
| 99/1 | 13.78 | 95.0 | 13.67 | 94.3 | 0.8% |
| 70/30 | 14.24 | 98.2 | 13.72 | 94.6 | 3.7% |
| 60/40 | 13.77 | 94.9 | 12.53 | 86.4 | 9.0% |
| 59/41 | 13.71 | 94.5 | 12.39 | 85.4 | 9.6% |
| 58/42 | 13.66 | 94.2 | 12.25 | 84.5 | 10.3% |
| HFC-63-14mcee/1,1,1,3,3,3-hexafluoro-2-propanol (58.7° C.) | | | | | |
| 14.5/85.5 | 14.68 | 101.2 | 14.68 | 101.2 | 0.0% |
| 5/95 | 14.62 | 100.8 | 14.61 | 100.7 | 0.1% |
| 1/99 | 14.55 | 100.3 | 14.54 | 100.3 | 0.1% |
| 30/70 | 14.55 | 100.3 | 14.47 | 99.8 | 0.5% |
| 50/50 | 14.10 | 97.2 | 13.63 | 94.0 | 3.3% |

TABLE 16-continued

| Composition (wt % A/wt % B) | Initial P (Psia) | Initial P (kPa) | After 50% Leak (Psia) | After 50% Leak (kPa) | Delta P (%) |
|---|---|---|---|---|---|
| 60/40 | 13.77 | 94.9 | 12.86 | 88.7 | 6.6% |
| 64/36 | 13.61 | 93.8 | 12.36 | 85.2 | 9.2% |
| 65/35 | 13.57 | 93.6 | 12.20 | 84.1 | 10.1% |
| HFC-63-14mcee/(CF$_3$)$_2$CBrC(O)CF$_2$CF$_3$ (94.1° C.) | | | | | |
| 64.6/35.4 | 14.69 | 101.3 | 14.69 | 101.3 | 0.0% |
| 80/20 | 14.63 | 100.9 | 14.63 | 100.9 | 0.0% |
| 90/10 | 14.53 | 100.2 | 14.52 | 100.1 | 0.1% |
| 99/1 | 14.38 | 99.1 | 14.38 | 99.1 | 0.0% |
| 40/60 | 14.54 | 100.3 | 14.52 | 100.1 | 0.1% |
| 20/80 | 14.18 | 97.8 | 14.13 | 97.4 | 0.4% |
| 10/90 | 13.90 | 95.8 | 13.86 | 95.6 | 0.3% |
| 1/99 | 13.59 | 93.7 | 13.58 | 93.6 | 0.1% |
| HFC-63-14mcee/DMTP (90.0° C.) | | | | | |
| 6.2/93.8 | 11.89 | 82.0 | 11.89 | 82.0 | 0.0% |
| 1/99 | 11.89 | 82.0 | 11.89 | 82.0 | 0.0% |
| 0/100 | 11.89 | 82.0 | 11.89 | 82.0 | 0.0% |
| 20/80 | 11.91 | 82.1 | 11.91 | 82.1 | 0.0% |
| 40/60 | 11.98 | 82.6 | 11.98 | 82.6 | 0.0% |
| 60/40 | 12.12 | 83.6 | 12.11 | 83.5 | 0.1% |
| 80/20 | 12.31 | 84.9 | 12.30 | 84.8 | 0.1% |
| 90/10 | 12.45 | 85.8 | 12.45 | 85.8 | 0.0% |
| 99/1 | 12.54 | 86.5 | 12.54 | 86.5 | 0.0% |
| 100/0 | 12.55 | 86.5 | 12.55 | 86.5 | 0.0% |
| HFC-63-14mcee/C$_4$F$_9$OCH$_3$/trans-DCE (50° C.) | | | | | |
| 1/98/1 | 10.84 | 74.7 | 10.53 | 72.6 | 2.9% |
| 1/1/98 | 16.05 | 110.7 | 15.94 | 109.9 | 0.7% |
| 20/20/60 | 16.79 | 115.8 | 16.70 | 115.1 | 0.5% |
| 10/10/80 | 16.73 | 115.4 | 16.63 | 114.7 | 0.6% |
| 30/30/40 | 16.47 | 113.6 | 15.81 | 109.0 | 4.0% |
| 40/20/40 | 16.37 | 112.9 | 15.67 | 108.0 | 4.3% |
| 20/40/40 | 16.59 | 114.4 | 16.01 | 110.4 | 3.5% |
| 20/50/30 | 16.13 | 111.2 | 14.91 | 102.8 | 7.6% |
| 50/10/40 | 16.28 | 112.2 | 15.62 | 107.7 | 4.1% |
| 60/1/39 | 16.20 | 111.7 | 15.57 | 107.4 | 3.9% |
| 65/1/34 | 16.09 | 110.9 | 15.00 | 103.4 | 6.8% |
| 68/1/31 | 16.00 | 110.3 | 14.46 | 99.7 | 9.6% |
| 1/80/19 | 15.27 | 105.3 | 13.97 | 96.3 | 8.5% |
| 1/83/16 | 14.83 | 102.2 | 13.40 | 92.4 | 9.6% |
| 1/84/15 | 14.66 | 101.1 | 13.20 | 91.0 | 10.0% |
| HFC-63-14mcee/C$_4$F$_9$OC$_2$H$_5$/trans-DCE (50° C.) | | | | | |
| 1/1/98 | 16.05 | 110.7 | 15.93 | 109.8 | 0.7% |
| 20/20/60 | 16.93 | 116.7 | 16.86 | 116.2 | 0.4% |
| 10/10/80 | 16.81 | 115.9 | 16.66 | 114.9 | 0.9% |
| 40/20/40 | 16.59 | 114.4 | 16.10 | 111.0 | 3.0% |
| 30/30/40 | 16.72 | 115.3 | 16.26 | 112.1 | 2.8% |
| 20/40/40 | 16.83 | 116.0 | 16.40 | 113.1 | 2.6% |
| 20/50/30 | 16.56 | 114.2 | 15.24 | 105.1 | 8.0% |
| 50/20/30 | 16.29 | 112.3 | 15.79 | 108.9 | 3.1% |
| 50/10/40 | 16.42 | 113.2 | 15.89 | 109.6 | 3.2% |
| 60/1/39 | 16.22 | 111.8 | 15.60 | 107.6 | 3.8% |
| 68/1/31 | 16.02 | 110.5 | 14.51 | 100.0 | 9.4% |
| 1/70/29 | 16.62 | 114.6 | 15.18 | 104.7 | 8.7% |
| 1/71/28 | 16.56 | 114.2 | 14.95 | 103.1 | 9.7% |

The mathematically predicted results show the difference in vapor pressure between the original composition and the composition remaining after 50 weight percent has been removed. Compositions of the invention have about a 10% or less difference between the vapor pressure of the original composition and the composition remaining after 50% has been removed.

Example 12

Distillation of a HFC-63-14mcee/trans-DCE composition

A solution containing about 20 weight percent HFC-63-14mcee and about 80 weight percent trans-1,2-dichloroethylene (trans-DCE) was prepared in a suitable container and mixed thoroughly. The solution was distilled in a five plate Oldershaw distillation column (7 cm diameter, 40 cm height) using a 10:1 reflux ratio. Head and pot temperatures were read directly to 1° C. The distillation was performed at a pressure of 760 mm Hg with about 30 minutes between cuts. Distillate compositions were determined by gas chromatography. Results are summarized in Table 17.

TABLE 17

| | Composition (weight percent) in cut | | Head |
|---|---|---|---|
| Sample | HFC-63-14mcee | Trans-DCE | temp (° C.) |
| Cut 1 | 24.03 | 75.97 | 45 |
| Cut 2 | 23.84 | 76.16 | 45 |
| Cut 3 | 23.48 | 76.52 | 45 |
| Cut 4 | 23.49 | 76.51 | 45 |
| Cut 5 | 23.62 | 76.38 | 45 |
| Heel | 17.07 | 79.71 | na |

Analysis of the above data indicates small differences in head temperatures and distillate compositions as the distillation progressed. A statistical analysis of the data demonstrates that the true azeotrope of HFC-63-14mcee and trans-DCE has the following characteristics at atmospheric pressure:

| HFC-63-14mcee | 23.7 ± 0.2 weight percent |
|---|---|
| Trans-DCE | 76.3 ± 0.2 weight percent |

Example 13

Distillation of a HFC-63-14mcee/ trans-DCE/ C$_4$F$_9$OC$_2$H$_5$ composition

A solution containing about 20 weight percent HFC-63-14mcee, about 60 weight percent trans-1,2-dichloroethylene (trans-DCE), and about 20 weight percent C$_4$F$_9$OC$_2$H$_5$ was prepared in a suitable container and mixed thoroughly. The solution was distilled in a five plate Oldershaw distillation column (7 cm diameter, 40 cm height) using a 10:1 reflux ratio. Head and pot temperatures were read directly to 1° C. The distillation was performed at a pressure of 760 mm Hg with about 30 minutes between cuts. Distillate compositions were determined by gas chromatography. Results are summarized in Table 18.

TABLE 18

| Sample | Composition (weight percent) in cut | | | Head temp (° C.) |
|---|---|---|---|---|
| | HFC-63-14mcee | Trans-DCE | $C_4F_9OC_2H_5$ | |
| Cut 1 | 11.14 | 72.96 | 15.90 | 44 |
| Cut 2 | 11.82 | 71.44 | 16.74 | 45 |
| Cut 3 | 12.44 | 70.57 | 16.99 | 45 |
| Cut 4 | 12.44 | 70.43 | 17.13 | 45 |
| Cut 5 | 12.55 | 70.38 | 17.07 | 45 |
| Heel | 30.49 | 43.63 | 25.88 | Na |

Analysis of the above data indicates small differences in head temperatures and distillate compositions as the distillation progressed. A statistical analysis of the data demonstrates that the true ternary azeotrope of HFC-63-14mcee, trans-DCE, and $C_4F_9OC_2H_5$ has the following characteristics at atmospheric pressure:

| | |
|---|---|
| HFC-63-14mcee | 12.1 ± 0.6 weight percent |
| Trans-DCE | 71.1 ± 1.0 weight percent |
| $C_4F_9OC_2H_5$ | 16.8 ± 0.5 weight percent |

Example 14

Solubility

Compositions of the present invention were tested for room temperature solubility with mineral oil, silicone oil (DC 200, Dow Corning, Midland, Mich.), and hydraulic fluid (mineral oil based). Solubility, in weight percent, was measured by weighing and placing an amount of fluid in a suitable container, then slowly adding a composition of the present invention until the fluid is completely dissolved. Results, in weight percent soluble, are shown in Table 19 below.

TABLE 19

| Composition (wt %) | Solubility (weight percent) | | | |
|---|---|---|---|---|
| | Mineral oil | DC 200 (5 cSt) | DC 200 (350 cSt) | Hydraulic Fluid |
| HFC-63-14mcee/trans-DCE (20/80) | 7 | na | na | na |
| HFC-63-14mcee/trans-DCE (24/76) | 4 | >88 | 13 | 4 |
| HFC-63-14mcee/trans-DCE/$C_4F_9OC_2H_5$ (13/70/17) | 17 | >90 | >90 | 17 |
| HFC-63-14mcee/trans-DCE/$C_4F_9OCH_3$ (5/40/55) | 11 | >90 | >90 | 11 |
| HFC-63-14mcee/trans-DCE/$C_4F_9OC_2H_5$/MeOH (8/68/16/8) | 29 | >90 | >90 | 27 |

The above data illustrates the usefulness of the present compositions for removing different types of oil residues.

Example 15

Defluxing Performance

Following the procedure of Example 7, the defluxing efficiency of the HFC-63-14mcee/trans-DCE azeotrope was tested using Alpha 611F RMA flux.

The residual ionics found on the board are given in Table 20.

TABLE 20

| Composition (wt %) | Board # | Residual Ionics (µgrams NaCl/sq in) Flux - Alpha 611F (RMA) |
|---|---|---|
| HFC-63-14mcee/trans-DCE (24/76) | 1 | 26.3 |
| | 2 | 49.8 |
| | 3 | 28.7 |
| | 4 | 30.0 |
| | 5 | 30.0 |
| | AVG | 33.2 |

Example 16

Cleaning

The compositions of the present invention are effective for cleaning ionic contamination (flux residue) from a surface. A similar procedure to the one described for Example 15 was used to apply the residue and then remove it from the surface. The cleaning ability was determined by weighing the board prior to deposition of the flux, after the deposition of the flux and then after the cleaning procedure.

The results for Alpha 611F RMA are given in Table 21.

TABLE 21

| Composition (wt %) | Dry weight (grams) | Wet weight (grams) | Post dry weight (grams) | % soil removed |
|---|---|---|---|---|
| HFC-63-14mcee/trans-DCE (24/76) | 21.4973 | 21.5065 | 21.4976 | 97% |
| | 21.4113 | 21.4211 | 21.4116 | 97% |
| | 21.0752 | 21.0878 | 21.0755 | 98% |
| | 21.7601 | 21.7756 | 21.7604 | 98% |
| | 21.0745 | 21.0946 | 21.0752 | 97% |
| | | Average | | 97% |

Example 17

Metal Cleaning Efficacy

Stainless steel (type 316) 2"×3" coupons that have been grit blasted to provide an unpolished surface were pre-cleaned and oven dried to remove any residual soil. Each coupon was weighed to 4 places to obtain a tare weight. A small amount of mineral oil was applied with a swab, the coupon is then weighed to obtain the "loaded" weight. The coupon was then cleaned by immersion into a boiling cleaning composition for 1 minute, held in vapor for 30 seconds and then air dried for 1 minute. The coupon was then weighed and the percent of soil removed is calculated using the 3 recorded weights. The results are shown in Table 22.

TABLE 22

| Composition (wt %) | Dry weight (grams) | Wet weight (grams) | Post Dry weight (grams) | Percent Soil removed |
|---|---|---|---|---|
| HFC-63-14mcee/ trans-DCE (24/76) | 21.4973 | 21.5065 | 21.4976 | 97 |
| | 21.4113 | 21.4211 | 21.4116 | 97 |
| | 21.0752 | 21.0878 | 21.0755 | 98 |
| | 21.7601 | 21.7756 | 21.7604 | 98 |
| | 21.0745 | 21.0946 | 21.0752 | 97 |
| | | Average | | 97 |
| HFC-63-14mcee/ $C_4F_9OC_2H_5$/ trans-DCE (13/17/70) | 21.4974 | 21.5133 | 21.4976 | 99 |
| | 21.7600 | 21.7730 | 21.7602 | 98 |
| | 21.4112 | 21.4206 | 21.4114 | 98 |
| | 21.0750 | 21.0957 | 21.0752 | 99 |
| | 21.5529 | 21.5724 | 21.5531 | 99 |
| | | Average | | 99 |

The results show efficient removal of mineral oil residue from stainless steel surfaces by the compositions of the present invention.

Example 18

Flammability

The flammability of the compositions of the present invention was evaluated by the Tag Closed Cup (ASTM D-56-82) test. The results are given in Table 24.

TABLE 23

| Composition | Flash point |
|---|---|
| HFC-63-14mcee/trans-DCE/ $C_4F_9OC_2H_5$ (13/70/17) | No flash point |
| HFC-63-14mcee/trans-DCE/ $C_4F_9OC_2H_5$/MeOH (8/68/16/8) | No flash point |

What is claimed is:

1. An azeotropic or azeotrope-like composition comprising:
   a. HFC-63-14mcee;
   b. trans-1,2-dichloroethylene; and
   c. at least one alcohol selected from the group consisting of methanol, ethanol, and isopropanol.

2. The composition of claim 1, wherein said azeotropic or azeotrope-like composition is selected from the group consisting of:
   a. from about 1 weight percent to about 40 weight percent of HFC-63-14mcee, from about 55 weight percent to about 94 weight percent trans-1,2-dichloroethylene, and from about 1 weight percent to about 30 weight percent methanol;
   b. from about 1 weight percent to about 40 weight percent of HFC-63-14mcee, from about 55 weight percent to about 94 weight percent trans-1,2-dichloroethylene, and from about 1 weight percent to about 30 weight percent ethanol; and
   c. from about 1 weight percent to about 40 weight percent of HFC-63-14mcee, from about 55 weight percent to about 94 weight percent trans-1,2-dichloroethylene, and from about 1 weight percent to about 30 weight percent isopropanol.

3. The composition of claim 1, wherein said composition is an azeotrope selected from the group consisting of:
   a. 18.7 weight percent HFC-63-14mcee, 73.2 weight percent trans-1,2-dichloroethylene, and 8.1 weight percent methanol having a vapor pressure of about 14.7 psia (101 kPa) at a temperature of about 40° C.;
   b. 21.8 weight percent HFC-63-14mcee, 73.8 weight percent trans-1,2-dichloroethylene, and 4.4 weight percent ethanol having a vapor pressure of about 14.7 psia (101 kPa) at a temperature of about 45° C.; and
   c. 22.5 weight percent HFC-63-14mcee, 75.0 weight percent trans-1,2-dichloroethylene, and 2.5 weight percent isopropanol having a vapor pressure of about 14.7 psia (101 kPa) at a temperature of about 45° C.

4. A process for removing residue from a surface or substrate, comprising:
   a. contacting the surface or substrate with the composition of claims 1, 2, or 3, and
   b. recovering the surface or substrate from the composition.

5. An azeotropic or azeotrope-like composition comprising:
   about 1 to about 68 weight percent HFC-63-14mcee and about 99 to about 32 weight percent trans-1,2-dichloroethylene.

6. The composition of claim 5, wherein said composition is an azeotrope comprising:
   24.0 weight percent HFC-63-14mcee and 76.0 weight percent trans-1,2-dichloroethylene having a vapor pressure of about 14.7 psia (101 kPa) at a temperature of about 45.0° C.

7. A process for removing residue from a surface, comprising:
   a. contacting the surface with the composition of claim 5 or 6, and
   b. recovering the surface from the composition.

8. The process of claim 7 wherein said residue comprises an oil.

9. The process of claim 7 wherein said residue comprises a rosin flux.

10. The process of claim 7 wherein the surface is an integrated circuit device.

11. The composition of claim 5, or 6, further comprising a stabilizer, a water scavenger, and/or an odor masking agent.

12. The composition of claim 11 wherein said stabilizer is selected from the group consisting of nitromethane, hindered phenols, hydroxylamines, thiols, phosphites and lactones.

13. The composition of claim 11 wherein said water scavenger is an ortho ester.

14. The composition of claim 1, 2, 5 or 6 further comprising an aerosol propellant.

15. The composition of claim 14 further comprising an aerosol propellant selected from the group consisting of air, nitrogen, carbon dioxide, dimethylether, difluoromethane, trifluoromethane, difluoroethane, trifluoroethane, tetrafluoroethane, pentafluoroethane, heptafluoropropane, and pentafluoropropane.

16. The composition of claim 5 or 6 further comprising at least one ultra-violet fluorescent dye selected from the group consisting of naphthalimides, perylenes, coumarins, anthracenes, phenanthracenes, xanthenes, thioxanthenes, naphthoxanthenes, fluoresceins, derivatives of said dye and combinations thereof.

17. The composition of claim 16, further comprising at least one solubilizing agent selected from the group consisting of hydrocarbons, dimethylether, polyoxyalkylene glycol ethers, amides, ketones, nitriles, chlorocarbons, esters, lactones, aryl ethers, hydrofluoroethers, and 1,1,1-trifluoroalkanes; and wherein the refrigerant and solubilizing agent are not the same compound.

18. The composition of claim 17, wherein said solubilizing agent is selected from the group consisting of:

a) polyoxyalkylene glycol ethers represented by the formula $R^1[(OR^2)_xOR^3]_y$, wherein: x is an integer from 1 to 3; y is an integer from 1 to 4; $R^1$ is selected from hydrogen and aliphatic hydrocarbon radicals having 1 to 6 carbon atoms and y bonding sites; $R^2$ is selected from aliphatic hydrocarbylene radicals having from 2 to 4 carbon atoms; $R^3$ is selected from hydrogen, and aliphatic and alicyclic hydrocarbon radicals having from 1 to 6 carbon atoms; at least one of $R^1$ and $R^3$ is selected from said hydrocarbon radicals; and wherein said polyoxyalkylene glycol ethers have a molecular weight of from about 100 to about 300 atomic mass units;

b) amides represented by the formulae $R^1C(O)NR^2R^3$ and cyclo-$[R^4C(O)N(R^5)-]$, wherein $R^1$, $R^2$, $R^3$ and $R^5$ are independently selected from aliphatic and alicyclic hydrocarbon radicals having from 1 to 12 carbon atoms, and at most one aromatic radical having from 6 to 12 carbon atoms; $R^4$ is selected from aliphatic hydrocarbylene radicals having from 3 to 12 carbon atoms; and wherein said amides have a molecular weight of from about 100 to about 300 atomic mass units;

c) ketones represented by the formula $R^1C(O)R^2$, wherein $R^1$ and $R^2$ are independently selected from aliphatic, alicyclic and aryl hydrocarbon radicals having from 1 to 12 carbon atoms, and wherein said ketones have a molecular weight of from about 70 to about 300 atomic mass units;

d) nitriles represented by the formula $R^1CN$, wherein $R^1$ is selected from aliphatic, alicyclic or aryl hydrocarbon radicals having from 5 to 12 carbon atoms, and wherein said nitriles have a molecular weight of from about 90 to about 200 atomic mass units;

e) chlorocarbons represented by the formula $RCl_x$, wherein x is 1 or 2; R is selected from aliphatic and alicyclic hydrocarbon radicals having from 1 to 12 carbon atoms; and wherein said chlorocarbons have a molecular weight of from about 100 to about 200 atomic mass units;

f) aryl ethers represented by the formula $R^1OR^2$, wherein: $R^1$ is selected from aryl hydrocarbon radicals having from 6 to 12 carbon atoms; $R^2$ is selected from aliphatic hydrocarbon radicals having from 1 to 4 carbon atoms; and wherein said aryl ethers have a molecular weight of from about 100 to about 150 atomic mass units;

g) 1,1,1-trifluoroalkanes represented by the formula $CF_3R^1$, wherein $R^1$ is selected from aliphatic and alicyclic hydrocarbon radicals having from about 5 to about 15 carbon atoms;

h) fluoroethers represented by the formula $R^1OCF_2CF_2H$, wherein $R^1$ is selected from aliphatic and alicyclic hydrocarbon radicals having from about 5 to about 15 carbon atoms; or wherein said fluoroethers are derived from fluoro-olefins and polyols, wherein said fluoro-olefins are of the type $CF_2=CXY$, wherein X is hydrogen, chlorine or fluorine, and Y is chlorine, fluorine, $CF_3$ or $OR_f$, wherein $R_f$ is $CF_3$, $C_2F_5$, or $C_3F_7$; and said polyols are of the type $HOCH_2CRR'(CH_2)_z(CHOH)_xCH_2(CH_2OH)_y$, wherein R and R' are hydrogen, $CH_3$ or $C_2H_5$, x is an integer from 0-4, y is an integer from 0-3 and z is either zero or 1; and i) lactones represented by structures [B], [C], and [D]:

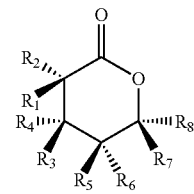

[B]

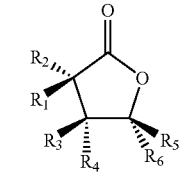

[C]

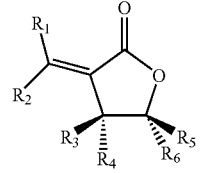

[D]

wherein, $R_1$ through $R_8$ are independently selected from hydrogen, linear, branched, cyclic, bicyclic, saturated and unsaturated hydrocarbyl radicals; and the molecular weight is from about 100 to about 300 atomic mass units; and j) esters represented by the general formula $R^1C(O)OR^2$, wherein $R^1$ and $R^2$ are independently selected from linear and cyclic, saturated and unsaturated, alkyl and aryl radicals; and wherein said esters have a molecular weight of from about 80 to about 550 atomic mass units.

* * * * *